United States Patent [19]
Powell et al.

[11] Patent Number: 5,856,127
[45] Date of Patent: Jan. 5, 1999

[54] ANTIMICROBIAL PEPTIDES

[75] Inventors: William Allen Powell; Charles A. Maynard, both of Syracuse, N.Y.

[73] Assignee: The Research Foundation of State University of New York, Albany, N.Y.

[21] Appl. No.: 686,594

[22] Filed: Jul. 26, 1996

[51] Int. Cl.[6] .................................................. C12P 21/00
[52] U.S. Cl. .................. 435/69.1; 435/69.3; 530/300; 530/350; 536/23.1; 800/205; 800/250; 935/88
[58] Field of Search ................... 435/69.1, 69.3, 435/810; 530/300, 350; 935/88; 800/200, 205, 250

[56] References Cited

U.S. PATENT DOCUMENTS

| | | | |
|---|---|---|---|
| 5,428,147 | 6/1995 | Logemann et al. | 536/24.1 |
| 5,451,514 | 9/1995 | Boudet et al. | 435/172.3 |
| 5,516,671 | 5/1996 | Lawrence et al. | 435/172.3 |
| 5,607,914 | 3/1997 | Rao et al. | 514/12 |

OTHER PUBLICATIONS

Agerberth, B., et al., Eur J Biochem 202: 849–854 (1991).
ASM News, vol. 60, No. 8, pp. 412–413 (1994).
Bessalle, R., et al., J Med Chem 36: 1203–1209 (1993).
Bevins, C.L., et al., Annu Rev. Biochem 59: 395–414 (1990).
Blondelle, S.E., et al., Biochemistry 30: 4671–4678 (1991).
Boman, H.G., et al., FEBS Letters 259(1): 103–106 (1989).
Broekaert, W.F., et al., Biochemistry 31: 4308–4314 (1992).
Campbell, W.H., et al., Plant Physiol 92: 1–11 (1990).
Chen, H.–C., et al., FEBS Letters 236(2): 462–466 (1988).
Christensen, B., et al., Proc Natl Acad Sci USA 85: 5072–5076 (1988).
Cornelissen, B.J.C., et al., Plant Physiol 101: 709–712 (1993).
Soravia, E., et al., FEBS Letters 228(2): 337–340 (1988).
Zasloff, M., Proc Natl Acad Sci USA 84:5449–5453 (1987).
Powell et al. (1995) Molecular Plant–Microbe Interactions, vol. 8, No. 5, pp. 792–794.
*Biochemistry* by Lehninger, A. [Worth Publishers, Inc., New York, NY, USA (1970)], p. 71.

*Primary Examiner*—Ardin H. Marschel
*Attorney, Agent, or Firm*—Jaeckle Fleischmann & Mugel, LLP; Susan J. Braman, Esq.

[57] ABSTRACT

The present invention is directed to antimicrobial polypeptides and to nucleic acid molecules encoding these antimicrobial polypeptides. The polypeptide consists of from 15 to 20 amino acids and has an amphipathic alpha helix structure, wherein 3 or more of the amino acids form a positively charged domain extending axially along the alpha helix. Expression vectors, host cells, and transgenic plants, as well as methods of producing plants having improved resistance to fungal and bacterial infestation, are also provided.

44 Claims, 1 Drawing Sheet

ANTIMICROBIAL PEPTIDES

This work was supported by the United States Department of Agriculture Grant Nos. USDA #96 CRMS 06102 USDA #CSRSOD-1088 and USDA #95373032083. The Federal Government may retain certain rights in the invention.

FIELD OF THE INVENTION

The present invention relates to antimicrobial polypeptides, nucleic acid molecules encoding these polypeptides, and their uses.

BACKGROUND OF THE INVENTION

Throughout this application various publications are referenced, many in parenthesis. Full citations for these publications are provided at the end of the Detailed Description of the Invention. The disclosures of these publications in their entireties, as well as those of U.S. Patents referenced herein, are hereby incorporated by reference in this application.

Disease resistance is an important objective of the genetic engineering of crop plants. Numerous fungi, bacteria, and other microbes are serious pests of common agricultural and forest crops. One method of controlling plant diseases has been to apply antimicrobial organic or semiorganic chemicals to crops. This method has numerous, art-recognized problems, such as pollution of surrounding environment causing harm to humans and nontarget, beneficial organisms. A more recent method of control of microorganism pests in plants has been the use of biological control organisms which are typically natural competitors or inhibitors of the troublesome microorganisms. However, it is difficult to apply biological control organisms to large areas, and even more difficult to cause those living organisms to remain in the treated area for an extended period. Still more recently, techniques in recombinant DNA have provided the opportunity to insert into plant cells cloned genes which express antifungal compounds. This technology has given rise to additional concerns about eventual microbial resistance to well-known, naturally occurring antifungals, particularly in the face of heavy selection pressure which may occur in some areas. Thus, a continuing effort is underway to express naturally occurring antifungal compounds in plant cells directly by translation of a single structural gene. However, there is a limited pool of naturally occurring peptides and other compounds with which molecular biologists can work. Attention is now focused on the rational design of entirely new peptides which can function effectively in plant cell expression systems and in other uses where antifungal peptides can be useful.

A steadily increasing interest is being focused on defense peptides produced by a variety of organisms (Cornelissen and Melchers 1993). These peptides or their analogs have the potential as a new source for disease resistant genes. Most of these small, lytic, antimicrobial peptides have been placed into four chemically distinct groups: the magainins, the cecropins, the defensins, and the proline-rich peptides (Agerberth et al. 1991).

The cecropins, first isolated from the cecropia moth, but recently from many insects, range from 26–37 amino acids in length. Their structure includes two α-helical regions, one amphiphilic and one hydrophobic, joined by a hinge region (Christensen et al. 1988). The cecropins are thought to produce single-channel conductances in lipid bilayers such as in a cell membrane (Wade et al. 1990). Most of these peptides described to date also demonstrate a specificity to microorganisms. One exception is melittin, isolated from bee venom. This peptide is very lytic to both microorganisms and animal red blood cells. The specificity of melittin can be altered by inverting the α-helical regions or by producing cecropin A/melittin hybrids (Boman et al. 1989). Amino acid omission studies on melittin showed that deletions in the α-helical regions decreased hemolytic activity but deletions in the "hinge" region did not (Blondelle and Houghten 1991).

The magainins, from the skin of the African clawed frog (Xenopus laevus), are some of the smallest natural antimicrobial peptides yet discovered, ranging from 21–27 amino acids in length (Zasloff 1987 and Bevins and Zasloff 1990). These peptides form an amphipathic, single α-helix which can span a cell membrane. It is hypothesized that these molecules form ion channels in the microbial cell's membrane which the cell cannot control, eventually leading to lysis of the cell. The α-helix is essential for activity and changes in the amino acid sequence which stabilize this helical structure enhance the molecule's lytic activity against selected bacteria (Chen et al. 1988).

The magainins are of interest because of their ability to lyse bacterial and yeast cells but not animal cells (Soravia et al. 1988), suggesting good potential for use in agricultural and forest plant species. Different peptides from this group also demonstrated synergistic effects. When the peptide PGLa was combined with either magainin I or magainin II in a 1:1 molar ratio, the antimicrobial activity increased 20–50 fold. Interestingly, alone these peptides had no hemolytic effect but in combination they exhibited the ability to lyse a variety of eukaryotic cells (Bevins and Zasloff 1990). This complementation demonstrated synergistic effects which should be considered when studying combinations of these types of peptides.

Although all the peptides in the magainins group have similar amphipathic α-helical structures, small differences in their amino acid sequences result in different antimicrobial activity. One example of this difference can be discerned by comparing the reported activities of PGLa and XPF (Soravia et al. 1988). These two peptides are very similar in terms of structure. When tested against the bacteria Pseudomonas aeruginosa, PGLa was 4–5 times more active than XPF. When these two were tested against the yeast Candida albicans, however, XPF was 2–2.5 times more effective than PGLa. Similar differences could also be seen among different species of bacteria (Soravia et al. 1988). Even a three amino acid substitution in $(Ala^{8,13,15})$magainin II, which is reported to increase helical stability, caused a change in activities on bacterial strains (Chen et al. 1988). Applicants have observed that these structural changes increased magainin activity against bacteria but had the opposite effect against selected filamentous fungi. This indicated for the first time that the ratios of activity between different organisms could potentially be manipulated.

However, to design peptides with a differential in vitro activity between plant and fungal cells, an understanding of the structural differences between melittin, the cecropins, and magainins and how they effect antimicrobial activity was needed.

Thus, a need continues to exist for new antimicrobial polypeptides useful in improving disease resistance in plants.

SUMMARY OF INVENTION

This need is met by the subject invention. More particularly, the present invention provides an isolated nucleic acid molecule encoding a polypeptide. The polypeptide is antimicrobial, consists of from 15 to 20 amino acids, and has an amphipathic alpha helix structure. Three or more of the amino acids of the polypeptide form a positively charged domain extending axially along the alpha helix.

The present invention also relates to an isolated nucleic acid molecule encoding a polypeptide, wherein the polypeptide comprises or includes an amino acid sequence of 15+q amino acid residues. In this polypeptide, residues number n, n+7, n+10, and n+14 are positively charged amino acids. In addition, at least one of residues number n, n+7, n+10, and n+14 is arginine, and the remaining amino acid residues are nonpolar amino acids or uncharged polar amino acids. n is an integer from 1 to 1+q, and q is 0, 1, 2, 3, 4, or 5.

The present invention further relates to an isolated nucleic acid molecule encoding a polypeptide, wherein the polypeptide comprises or includes an amino acid sequence of 15+q amino acid residues. The residues number n, n+6, n+7, n+10, n+13, and n+14 are positively charged amino acids, and the remaining amino acid residues are nonpolar amino acids or uncharged polar amino acids. n is an integer from 1 to 1+q, and q is 0, 1, 2, 3, 4, or 5.

The present invention also relates to an isolated nucleic acid molecule encoding a polypeptide, wherein the polypeptide comprises or includes an amino acid sequence of 15+q amino acid residues. Residues number n, n+7, and n+14 are positively charged amino acids, and the remaining amino acid residues are nonpolar amino acids. n is an integer from 1 to 1+q, and q is 0, 1, 2, 3, 4, or 5.

The present invention, in another aspect thereof, relates to an isolated nucleic acid molecule encoding a polypeptide, wherein the polypeptide comprises or includes an amino acid sequence of 15+q amino acid residues. The residues number n, n+7, and n+10 are positively charged amino acids, and the remaining amino acid residues are nonpolar amino acids. n is an integer from 1 to 5+q, and q is 0, 1, 2, 3, 4, or 5.

Another aspect of the present invention relates to a polypeptide consisting of from 15 to 20 amino acids. The polypeptide is an antimicrobial and has an amphipathic alpha helix structure. Three or more of the amino acids of the polypeptide form a positively charged domain extending axially along the alpha helix.

The present invention also relates to a polypeptide comprising an amino acid sequence of 15+q amino acid residues. The residues number n, n+7, n+10, and n+14 are positively charged amino acids, and at least one of amino acids number n, n+7, n+10, and n+14 is arginine, and the remaining amino acids are nonpolar amino acids or uncharged polar amino acids. n is an integer from 1 to 1+q, and q is 0, 1, 2, 3, 4, or 5.

The present invention further relates to a polypeptide comprising an amino acid sequence of 15+q amino acid residues. The residues number n, n+6, n+7, n+10, n+13, and n+14 are positively charged amino acids, and the remaining amino acid residues are nonpolar amino acids or uncharged polar amino acids. n is an integer from 1 to 1+q, and q is 0, 1, 2, 3, 4, or 5.

In another aspect of the present invention, a polypeptide comprising an amino acid sequence of 15+q amino acid residues is provided. The residues number n, n+7, and n+14 are positively charged amino acids, and the remaining amino acid residues are nonpolar amino acids. n is an integer from 1 to 1+q, and q is 0, 1, 2, 3, 4, or 5.

The present invention also provides a polypeptide comprising an amino acid sequence of 15+q amino acid residues.

The residues number n, n+7, and n+10 are positively charged amino acids, and the remaining amino acid residues are nonpolar amino acids. n is an integer from 1 to 5+q, and q is 0, 1, 2, 3, 4, or 5.

The isolated nucleic acid molecules of the invention can be inserted into suitable expression vectors and/or host cells. Expression of the nucleic acid molecules encoding the subject polypeptide results in production of the subject polypeptide in a host cell. The present invention further provides transgenic plants and seeds which contain nucleic acid molecules encoding the subject polypeptide.

Another aspect of the present invention relates to a method of producing a plant having improved resistance to fungal or bacterial infestation. The method includes introducing a nucleic acid molecule encoding the subject polypeptide into a plant cell and culturing the plant cell under conditions effective for expression of the nucleic acid molecule. The present invention further provides a method of producing a plant cell useful for regeneration of a plant having increased fungal or bacterial resistance. The method includes transforming a plant cell with a nucleic acid molecule encoding the subject polypeptide.

BRIEF DESCRIPTION OF THE DRAWING

These and other features and advantages of this invention will be evident from the following description of preferred embodiments when read in conjunction with the accompanying drawing in which.

DETAILED DESCRIPTION OF THE INVENTION

Figure 1:
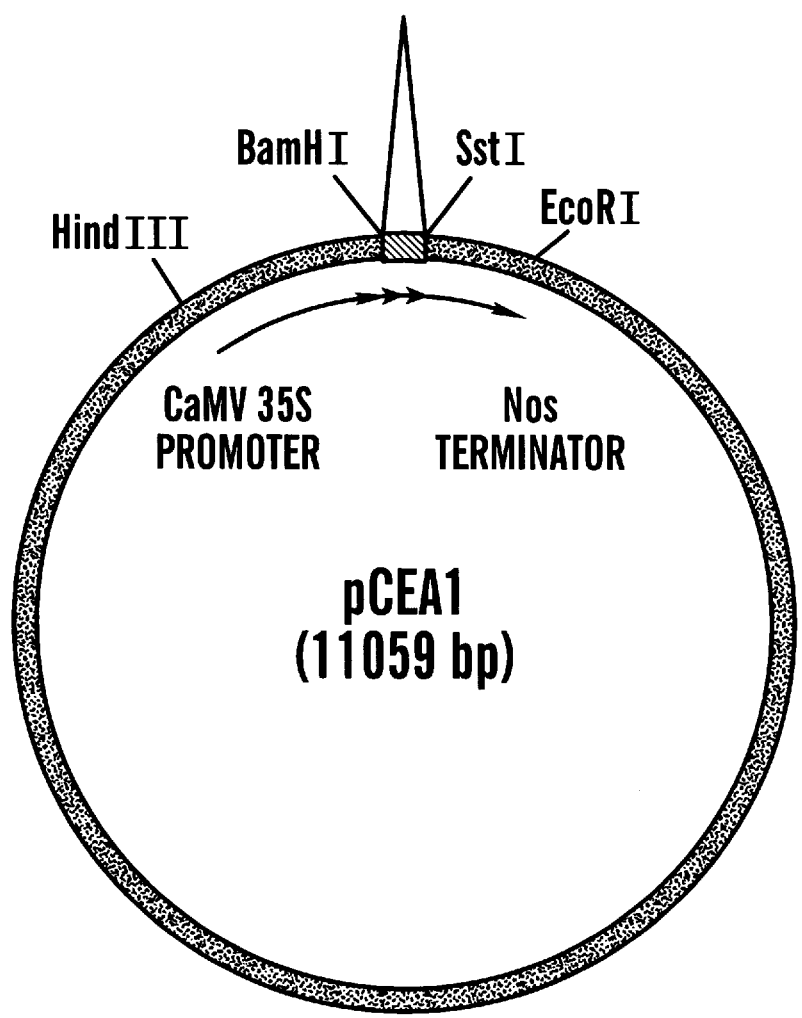
FIG. 1 is a plasmid map of the plasmid designated pCEA1.

The present invention relates to an isolated nucleic acid molecule encoding an antimicrobial polypeptide which consists of from 15 to 20 amino acids and which has an amphipathic alpha helix structure. Three or more of the amino acids form a positively charged domain which extends axially along the alpha helix.

Polypeptide chains form by condensation of two or more amino acid residues. In this process, the acid end of a first amino acid reacts with the amino end of a second amino acid, eliminating water, and forming a peptide bond in which the acid carbon becomes covalently bonded to the amine nitrogen. The resulting dipeptide, having both an acid as well as an amine terminus, can go on to react with a third amino acid, at either its carboxyl or amino end, to form a tripeptide. Further repetition of the process produces a polypeptide. Like the dipeptide and tripeptide, the polypeptide has an acid group at one end and an amine group at the other end. These ends are commonly referred to as the C-terminus (carboxy terminus) and the N-terminus (amino terminus) of the polypeptide.

Individual extended polypeptide chains are conformationally unstable and frequently either assume contracted helical configurations or aggregate side by side to form sheet-like structures. The driving force that leads to either of these two alternatives is the strong tendency of the carbonyl and imino groups that flank the peptide bonds to form non-covalent, hydrogen bonds. When the carbonyl group next to one peptide bond hydrogen-bonds to an imino group flanking another peptide bond several residues removed from it on the same chain, a highly repetitive, regular polypeptide conformation results. This folding pattern causes the polypeptide to assume a secondary structure known as the alpha helix. The likelihood that a particular polypeptide will form an alpha helix can be predicted from the polypeptide's primary amino acid sequence using, for example, Garnier-Robson (Garnier et al. 1978) or Chou-Fasman (Chou and Fasman 1978) algorithims within a Lasergene or PROTEAN program (DNASTAR, Inc., Madison, Wis.).

As used herein to describe the alpha helix of the polypeptide of the present invention, amphipathic means that the amino acid residues of the polypeptide are aligned three dimensionally to form both hydrophilic and hydrophobic regions. Preferably the polypeptide contains an amphipathic alpha helix structure as predicted by the Eisenberg Moment (Eisenberg et al. 1984).

As used herein, two or more positively charged amino acid residues of the polypeptide, when located in spatial proximity to one another, can form a positively charged domain. The spatial proximity can be achieved when the two positively charged amino acids are consecutive (in terms of primary structure). In this case, the positively charged domain extends circumferentially around the alpha helix. Alternatively, the spatial proximity of two or more positively charged amino acids can be achieved when the two residues lie in adjacent (or nearly adjacent) coils of the alpha helix. In this case, the positively charged domain extends axially, that is, in a direction parallel to the axis of the alpha helix. Likewise, two or more negatively charged amino acid residues can form a negatively charged domain.

Antimicrobial, as used herein to describe the polypeptides of the present invention, means that the polypeptide has the capacity to kill, disrupt reproduction, or otherwise disable microbial growth so that the polypeptide has a minimal inhibitory concentration ("MIC") of less than 250 $\mu$M, preferably less than 50 $\mu$M, more preferably less than 20 $\mu$M. The procedures for determining MIC of an antimicrobial polypeptide are known to those skilled in the art and are described in the Materials and Methods section below and in Powell et al. 1995. It is contemplated that, for purposes of the present invention, a polypeptide is an antimicrobial if it has the aforementioned MIC with respect to any microbe. Microbes, as used herein, include fungi, such as *Cryphonectria parasitica, Fusarium oxysporum, Septoria musiva*, bacteria, especially plant-pathogenic bacteria, such as *Agrobacterium tumefaciens, Erwinia amylovoria*, and *Pseudomonas syringae*, as well as mycoplasmae, viruses, viroids, nematodes, protozoa, and the like.

As used herein, the term "isolated" when used in conjunction with a nucleic acid molecule refers to: 1) a nucleic acid molecule which has been separated from an organism or cell in a substantially purified form (i.e. substantially free of other substances originating from that organism or cell), 2) a nucleic acid molecule having the same nucleotide sequence but not necessarily separated from the organism (i.e. synthesized nucleic acid molecules), or 3) a synthetically produced nucleic acid molecule that does not occur in nature.

As further used herein, the terms "corresponding to" or "having" or "as shown in" or "consisting of" when used in conjunction with a SEQ ID NO for a nucleotide sequence refer to a nucleotide sequence which is substantially the same nucleotide sequence, or derivatives thereof (such as deletion and hybrid variants thereof, splice variants thereof, etc.). Nucleotide additions, deletions, and/or substitutions, such as those which do not affect the translation of the DNA molecule, are within the scope of a nucleotide sequence corresponding to or having or as shown in or consisting of a particular nucleotide sequence (i.e. the amino acid sequence encoded thereby remains the same). Such additions, deletions, and/or substitutions can be, for example, the result of point mutations made according to methods known to those skilled in the art, or alternatively the "altered" nucleotide sequence can be produced synthetically. It is also possible to substitute a nucleotide which alters the amino acid sequence encoded thereby, where the amino acid substituted is a conservative substitution or where amino acid homology is conserved. It is also possible to have minor nucleotide additions, deletions, and/or substitutions which do not alter the function of the resulting antimicrobial polypeptide. These are also within the scope of a nucleotide sequence corresponding to or having or as shown in or consisting of a particular nucleotide sequence.

Similarly, the term "corresponding to" or "having" or "as shown in" or "consisting of" when used in conjunction with a SEQ ID NO for an amino acid sequence refers to an amino acid sequence which is substantially the same amino acid sequence or derivatives thereof. Amino acid additions, deletions, and/or substitutions which do not negate the ability of the peptide to be antimicrobial are within the scope of an amino acid sequence corresponding to or having or as shown in or consisting of a particular amino acid sequence. Such additions, deletions, and/or substitutions can be, for example, the result of point mutations in the DNA encoding the amino acid sequence, such point mutations made according to methods known to those skilled in the art. Substitutions may be conservative substitutions of amino acids. Two amino acid residues are conservative substitutions of one another, for example, where the two residues are of the same type. In this regard, lysine, arginine, and histidine, all of which are positively charged residues, are of the same type. The weakly hydrophobic amino acids alanine, valine, isoleucine, glycine, cysteine, phenylalanine, tryptophan, and proline, and the strongly hydrophobic amino acids leucine and methionine, all of which are nonpolar amino acid residues, are of the same type. Another type of residue is the uncharged polar amino acid residue, which includes serine, threonine, tyrosine, asparagine, and glutamine. Yet another type of residue is the negatively charged amino acid residue, which includes aspartic acid and glutamic acid. Further descriptions of the concept of conservative substitutions are given by French and Robson 1983, Taylor 1986, and Bordo and Argos 1991.

As further used herein, the term "corresponding to" or "having" or "as shown in" or "consisting of" when used in conjunction with a SEQ ID NO for a nucleotide or amino acid sequence is intended to cover linear or cyclic versions of the recited sequence (cyclic referring to entirely cyclic versions or versions in which only a portion of the molecule is cyclic, including, for example, a single amino acid cyclic upon itself), and is intended to cover derivative or modified nucleotide or amino acids within the recited sequence. For example, those skilled in the art will readily understand that an adenine nucleotide could be replaced with a methyladenine, or a cytosine nucleotide could be replaced with a methylcytosine, if a methyl side chain is desirable. Nucleotide sequences having a given SEQ ID NO are intended to encompass nucleotide sequences containing these and like derivative or modified nucleotides, as well as cyclic variations. As a further example, those skilled in the art will readily understand that an asparagine residue could be replaced with an ethylasparagine if an ethyl side chain is desired, a lysine residue could be replaced with a hydroxylysine if an OH side chain is desired, or a valine residue could be replaced with a methylvaline if a methyl side chain is desired. Amino acid sequences having a given SEQ ID NO are intended to encompass amino acid sequences containing these and like derivative or modified amino acids, as well as cyclic variations. Cyclic, as used herein, also refers to cyclic versions of the derivative or modified nucleotides and amino acids.

The nucleic acid molecule can be deoxyribonucleic acid ("DNA") or ribonucleic acid ("RNA"), the later including messenger RNA ("mRNA"). The nucleic acid can be recombinant, biologically isolated, or synthetic. The DNA molecule can be a cDNA molecule which is a DNA copy of an mRNA encoding the polypeptide of the present invention.

Preferably, the isolated nucleic acid molecule encodes a polypeptide consisting of 18 to 20 amino acids and having a methionine residue as its N-terminal amino acid.

As indicated above, the polypeptide encoded by the nucleic acid of the present invention can consist of between 15 and 20 amino acid residues. Where the number of amino acid residues in the polypeptide is q, suitable polypeptides include those where amino acid residues number n, n+7, and n+14 are each a positively charged amino acid. n can be any integer between 1 and q-14, inclusive. For example, nucleic acid molecules encoding polypeptides having positively charged amino acids at residues number 1, 8, and 15; 2, 9, and 16; 3, 10, and 17; 4, 11, and 18; or 5, 12, and 19, are within the scope of the present invention.

Alternatively, the present invention relates to nucleic acids encoding polypeptides whose amino acid residues number n, n+7, and n+10 are each positively charged where n can be any integer between 1 and q-10, inclusive, and q is the number of residues in the polypeptide. Thus,for example, nucleic acid molecules encoding polypeptides having positively charged amino acids at residues number 1, 8, and 11; or 2, 9, and 12; or 3, 10, and 13; or 4, 11, and 14; or 5, 12, and 15; or 6, 13, and 16; or 7, 14, and 17; or 8, 15, and 18; or 9, 16, and 19; or 10, 17, and 20 are also within the scope of the present invention.

The positively charged residues referred to above can be the same or different and are selected from the group consisting of lysine, arginine, and histidine. The remaining amino acid residues of the antimicrobial polypeptide are not critical to the practice of the present invention so long, of course, that their selection does not preclude the formation of an amphipathic alpha helix secondary structure. It is preferred, however, that at least nine amino acids of the polypeptide are nonpolar amino acids. The at least nine nonpolar amino acids of the polypeptide can be the same or different and are selected from the group consisting of alanine, valine, leucine, isoleucine, glycine, cysteine, phenylalanine, tryptophan, proline, and methionine. In a preferred embodiment, the antimicrobial polypeptide has a methionine as an N-terminal amino acid and at least seven of the nonpolar amino acids are alanine.

In one embodiment, the isolated antimicrobial polypeptide is encoded by the nucleotide sequence as shown in SEQ ID NO:15 and has an amino acid sequence as shown in SEQ ID NO:1. In other alternative embodiments of the present invention, suitable nucleic acid molecules include those which encode an amino acid sequence as shown in SEQ ID NO:2, SEQ ID NO:3, SEQ ID NO:4, SEQ ID NO:5, SEQ ID NO:6, SEQ ID NO. 7, SEQ ID NO:8, SEQ ID NO:9, SEQ ID NO:10, SEQ ID NO:11, SEQ ID NO:12, SEQ ID NO:13, or SEQ ID NO:14. Exemplary nucleic acids encoding antimicrobial polypeptides having amino acid sequences as shown in SEQ ID NO:3, SEQ ID NO:4, SEQ ID NO:10, SEQ ID NO:13, and SEQ ID NO:14 are those having nucleic acid sequences as shown in SEQ ID NO:16, SEQ ID NO:17, SEQ ID NO:18, SEQ ID NO:19, and SEQ ID NO:20, respectively.

In another, alternative embodiment, the isolated nucleic acid molecule of the present invention can encode a polypeptide which comprises an amino acid sequence of between 15 and 20 amino acid residues, four of which, namely n, n+7, n+10, and n+14, are positively charged amino acids, at least one of these positively charged amino acids being arginine. n, as used to describe the particular amino acid residue in the polypeptide, can be any integer from 1 to 1+q, where q is defined by the length of the amino acid sequence and can be 0, 1, 2, 3, 4, or 5. For example, when the amino acid sequence contains 20 amino acid residues, q is 5, and n can be 1, 2, 3, 4, 5, or 6. Thus, when q is 5, polypeptides of the present invention include those having positively charged amino acids at residues number 1, 8, 11, and 15 (n32 1); 2, 9, 12, and 16 (n=2); 3, 10, 13, and 17 (n=3); 4, 11, 14, and 18 (n=4); 5, 12, 15, and 19 (n=5); or 6, 13, 16, and 20 (n=6). The remaining amino acid residues of the amino acid sequence are nonpolar amino acids or uncharged polar amino acids.

In this embodiment, that is, where n, n+7, n+10, and n+14 are positively charged amino acids, each positively charged amino acid residue is preferably arginine. In addition, when n is 2, residue number 1 is preferably an uncharged polar amino acid, and, when n is 3 or greater, residue number 1 is preferably a strongly hydrophobic nonpolar amino acid and residue number n-1 is an uncharged polar amino acid. In either case, residues number n+4, n+8, n+11, n+13, and, if q-n is greater than or equal to 1, residue number n+16, are strongly hydrophobic nonpolar amino acids. The remaining amino acid residues are preferably weakly hydrophobic nonpolar amino acids. For example, when q is 5 and n is 4, each of the positively charged amino acids can be an arginine, residue number 1 can be a methionine, residue number 3 can be a serine, residue number 7 can be a glycine, each of residues number 8, 12, 15, 17, and 20 can be a leucine, and each of the remaining amino acids can be an alanine (see SEQ ID NO:3).

In another aspect of the present invention the isolated nucleic acid molecule encodes an antimicrobial polypeptide, which polypeptide comprises an amino acid sequence having between 15 and 20, inclusive, amino acid residues. Of these amino acid residues, 6 are positively charged amino acids. More particularly, the positively charged amino acids are residues number n, n+6, n+7, n+10, n+13, and n+14. n can be any integer from 1 to 1+q, where q is defined by the length of the amino acid sequence and can be 0, 1, 2, 3, 4, or 5. Thus, n can be any integer in the range from 1 to 6, inclusive. In one example, the amino acid sequence contains 20 amino acid residues so q is 5 and n can be 1, 2, 3, 4, 5, or 6. When q is 5, nucleic acid molecules encoding polypeptides having amino acid sequences containing positively charged amino acid residues at 1, 7, 8, 11, 14, and 15 (n=1); or 2, 8, 9, 12, 15, and 16 (n=2); or 3, 9, 10, 13, 16, and 17 (n=3); or 4, 10, 11, 14, 17, and 18 (n=4); or 5, 11, 12, 15, 18, and 19 (n=5); or 6, 12, 13, 16, 19, and 20 (n=6) are nucleic acid molecules illustrative of this embodiment.

Where the positively charged amino acid residues are n, n+6, n+7, n+10, n+13, and n+14, and when n is 2, residue number 1 is preferably an uncharged polar amino acid. On the other hand, when n is 3 or 4, it is preferred that residue number 1 be a strongly hydrophobic nonpolar amino acid and that residue number n-1 be an uncharged polar amino acid. In either case, residues number n+4, n+8, and n+11 are preferably strongly hydrophobic nonpolar amino acids, and the remaining amino acids are preferably weakly hydrophobic nonpolar amino acids. For example, in a preferred embodiment where q is 5 and n is 4, the positively charged amino acids are arginine, residue number 1 is methionine, residue number 3 is serine, residues number 8, 12, 15, and 20 are leucine, residue number 7 is glycine, and the remaining amino acid residues are each alanine (see SEQ ID NO:10).

In yet another aspect of the present invention, the isolated nucleic acid molecule of the present invention can encode a polypeptide which comprises an amino acid sequence of between 15 and 20 amino acid residues, three of which, namely n, n+7, and n+14, are positively charged amino acids, at least one of these positively charged amino acids being arginine. n, as used to describe the particular amino acid residue in the polypeptide, can be any integer from 1 to 1+q, where q is defined by the length of the amino acid sequence, that is, q can be 0, 1, 2, 3, 4, or 5. For example, when the amino acid sequence contains 20 amino acid residues, q is 5, and n can be 1, 2, 3, 4, 5, or 6. Thus, for example, when q is 5, polypeptides of the present invention include those having positively charged amino acids at residues number 1, 8, and 15 (n=1); 2, 9, and 16 (n=2); 3, 10, and 17 (n=3); 4, 11, and 18 (n=4); 5, 12, and 19 (n=5); or 6, 13, and 20 (n=6). The remaining amino acid residues of the amino acid sequence are nonpolar amino acids or uncharged polar amino acids.

In this embodiment, that is, where residues number n, n+7, and n+14 are positively charged amino acids, it is preferred that residues number n+4, n+8, n+11, and n+13 be strongly hydrophobic nonpolar amino acids. When n is an integer from 2 to 4, residue number 1 is preferably a strongly hydrophobic nonpolar amino acid, and the remaining amino acids are preferably weakly hydrophobic nonpolar amino acids. For example, when q is 5 and n is 4, each of the positively charged amino acids can be arginine, residue number 1 can be methionine, each of residues number 8, 12, 15, 17, and 20 can be leucine, residue number 7 can be glycine, and each of the remaining amino acids can be alanine (see SEQ ID NO:13).

In still another embodiment, the encoded polypeptide can comprise an amino acid sequence of between 15 and 20 amino acid residues, three of which, namely n, n+7, and n+10, are positively charged amino acids. Preferably, at least one of the three positively charged amino acids is arginine. n, as used to describe the particular amino acid residue in the polypeptide, can be any integer from 1 to 5+q, where q is defined by the length of the amino acid sequence, that is, q can be 0, 1, 2, 3, 4, or 5. For example, when the amino acid sequence contains 20 amino acid residues, i.e., when q is 5, n can be any integer from 1 to 10, inclusive. Thus, for example, when q is 5, polypeptides of the present invention include those containing amino acid sequences having positively charged amino acids at residues number 1, 8, and 11 (n=1); 2, 9, and 12 (n=2); 3, 10, and 13 (n=3); 4, 11, and 14 (n=4); 5, 12, and 15 (n=5); 6, 13, and 16 (n=6); 7, 14, and 17 (n=7); 8, 15, and 18 (n=8); 9, 16, and 19 (n=9); or 10, 17, and 20 (n=10). The remaining amino acid residues of the amino acid sequence are preferably either nonpolar amino acids or uncharged polar amino acids. More particularly, when q is 0 and n is 2, residue number 1 is preferably an uncharged polar amino acid; each of residues number 6, 13, and 15 is a strongly hydrophobic nonpolar amino acid; each of the remaining residues are weakly hydrophobic amino acids. Especially preferred are polypeptides containing amino acid sequences where q is 0 and n is 2 each of the positively charged amino acids is arginine, residue number 1 is serine; each of residues number 6, 10, 13, and 15 is leucine, residue number 5 is glycine, and each of the remaining amino acids is alanine (see SEQ ID NO:14).

In most cases, the antimicrobial polypeptides of the present invention are not known to occur in nature. Consequently, DNA molecules encoding the antimicrobial polypeptides must be designed and constructed. Optimal expression of the antimicrobial polypeptides requires taking into account several DNA molecule design considerations. These considerations are discussed below in the Materials and Methods section in the context of designing nucleic acid molecules encoding ESF12 (SEQ ID NO:1).

DNA molecules encoding the antimicrobial polypeptides can be prepared entirely by chemical synthetic means. Chemical synthesis of DNA molecules can be achieved through application of solution chemistries or, preferably, can be carried out on solid supports. These methods are well known to those skilled in the art and are described in detail, for example, in U.S. Pat. No. 5,519,115 to Mapelli et al.

The DNA molecule encoding the antimicrobial polypeptide of the present invention can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted peptide-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant nucleic acid molecules may also be introduced into viruses, such as vaccinia virus, and the resulting virus is used as a vector to transfer the recombinant nucleic acid molecule into a host cell (by infecting a host cell with the resulting virus vector).

Suitable vectors include, but are not limited to, viral vectors such as lambda vector system gt11, gt WES.tB, Charon 4, and plasmid vectors such as pBR322, pBR325, pACYC177, pACYC184, pUC8, pUC9, pUC18, pUC19, pUC118, pUC119, pLG339, pR290, pKC37, pKC101, pGEM (Promega), pCR (In Vitrogen), SV 40, pBluescript II SK ± or KS ± (see "Stratagene Cloning Systems" Catalog (1993) from Stratagene, La Jolla, Calif, which is hereby incorporated by reference), pQE, pIH821, PGEX, pET series (see Studier et al. 1990), and any derivatives thereof. Other vectors especially suitable for plant transformation include pBI101, pBI102, pBI103, pBI121, pBin19, pCGN566, pTi15955, pB1221, pGSC1700, pKYLX(71), and pGASCI (3 types).

Recombinant nucleic acid molecules can be introduced into cells via transformation, transduction, conjugation, mobilization, or electroporation, for example. The DNA sequences are cloned into the vector using standard cloning procedures in the art, as described by Sambrook et al. 1989.

A variety of host-vector systems may be utilized to express the peptide-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.);

insect cell systems infected with virus (e.g., baculovirus); and plant cells infected by bacteria or transformed via particle bombardment (i.e. biolistics). The expression elements of these vectors vary in their strength and specificities. Depending upon the host-vector system utilized, any one of a number of suitable transcription and translation elements can be used.

Once the isolated DNA molecules encoding the antimicrobial polypeptides, as described above, have been cloned into an expression system, they are ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The antimicrobial polypeptides of the present invention can be advantageously produced by either chemical synthesis or by one or more methods of inserting specific nucleic acid molecules encoding one or more of the polypeptides into a host cell and allowing that cell to express the desired polypeptide. With regard to traditional chemical synthesis, antimicrobial polypeptides in accordance with the present invention can be synthesized using any of the known peptide synthesis protocols such as those described in Gross and Meienhofer (1980) and Udenfriend and Meienhofer (1987). Further details relating to the chemical synthesis of the antimicrobial peptides of the present invention can be found, for example, in U.S. Pat. No. 5,519,115 to Mapelli et al. Alternatively, as indicated above, the antimicrobial polypeptides can be produced by common technology using host cells into which the nucleic acid molecules encoding the antimicrobial polypeptide have been introduced. The host cells are then cultured under conditions effective to functionally express the antimicrobial polypeptide, and subsequently, the antimicrobial polypeptide is isolated from the culture. Alternatively, the antimicrobial peptide can be produced in vivo in the host of interest, where its expression provides the desired antimicrobial protection of the host.

The antimicrobial polypeptides of the present invention can have wide use in a number of everyday situations where one desires to inhibit the growth or survival of microbes. In particular, the polypeptides of the present invention can be used to enhance crop yields by reducing the economic impact of crop destruction brought about by plant microbial pathogens. However, the polypeptides of the present invention may also be valuable as pharmaceutical agents in the treatment of human or animal disease caused by microbes, as additives to foodstuffs for the purpose of food preservation during storage or shipping, as domiciliary or medical disinfectants, or as preservatives in cosmetics, pharmaceuticals, or other products. The antimicrobial polypeptides of the present invention could be useful in all of these contexts either by themselves or in combination with other chemical or pharmaceutical compounds which are effective against microbial pathogens of humans, animals, or plants.

The polypeptides of the present invention can be effectively applied to plants afflicted with microbes such as bacteria, fungi, and the like, by any convenient means, including spray, dust, or other formulations common to the antimicrobial arts. The compound can also be incorporated systemically into the tissue of a treated plant so that in the course of infesting the plant the pathogens will be exposed to antimicrobial amounts of the polypeptide of the present invention. One method of doing this is to incorporate the compound in a non-phytotoxic vehicle which is adapted for systemic administration to the susceptible plants. This method is commonly employed with conventional fungicidal materials, such as Triazole fungicide, and is well within the skill of the ordinary art-worker.

Since the nucleic acid molecules which code for these antimicrobial polypeptides can be inserted into appropriate expression vectors and introduced into cells of a susceptible host, such as a plant, an especially preferred embodiment of the present invention relates to a method of producing a plant having improved resistance to fungal or bacterial infestation. The plant is preferably a plant susceptible to infection and damage by one or more microbes, such as C. parasitica, F. oxysporum, S. musiva, as well as other species of fungi, particularly filamentous fungi, as well as bacterial species, such as A. tumefaciens, E. amylovora, and P. syringae. These plant species include, for example, species of the genera Allium, Antirrhinum, Arabidopsis, Arachis, Asparagus, Atropa, Avena, Beta, Brassica, Browallia, Capsicum, Castanea, Cicer, Cicla, Citrullus, Citrus, Cucumis, Cucurbita, Datura Daucus, Digitalis, Fagopyrum, Fragaria, Geranium, Glycine, Gossypium, Helianthus, Hordeum, Hemerocallis, Lactuca, Lens, Lolium, Lotus, Lycopersicon, Majorana, Malus, Manihot, Medicago, Nasturtium, Nicotiana, Oryza, Pelargonium, Persea, Petunia, Phaseolus, Pisum, Prunus, Ranunculus, Raphanus, Ricinus, Saccharum, Salix, Secale, Senecio, Setaria, Solanum, Spinacia, Trifolium, Triticum, Bromus, Cichorium, Hyoscyamus, Linum, Nemesia, Panicum, Onobrychis, Pennisetum, Salpiglossis, Sinapis, Trigonella, and Vigna. This list is exemplary only, and the invention is not intended to be limited to these enumerated examples.

Common names of plants suitable for transformation according to the method of this invention include cereal crops, such as maize, rye, barley, wheat, sorghum, oats, millet, rice, triticale, sunflower, alfalfa, rapeseed, and soybean, as well as vegetable crops such as cabbage, tomato, potato, and radish, and fruit crops, such as grape and apple. In addition, the method of the present invention can be used to improve the resistance of trees, such as chestnut, poplar, elm, butternut, walnut, and the like.

Having exemplified the plants of interest, plant cells suitable for transformation include leaf segments, stem segments, root segments, meristems, immature embryos, calli, suspension cells, and protoplasts. It is particularly preferred to use explants and immature embryos. Transformation of plant cells can be accomplished by using a plasmid. The plasmid is used to introduce the nucleic acid encoding the antimicrobial polypeptide into the plant cell. Accordingly, a plasmid preferably includes DNA encoding the antimicrobial polypeptide inserted into a unique restriction endonuclease cleavage site. DNA is inserted into the plasmid vector using standard cloning procedures readily known in the art. This generally involves the use of restriction enzymes and DNA ligases as described by Sambrook (1989). Resulting plasmids which include nucleic acid encoding an antimicrobial polypeptide can then be used to transform a host cell, such as an Agrobacterium and/or plant cell. (See generally, Galvin and Schilperoort (1994).)

For plant transformation, the plasmid preferably also includes a selectable marker for plant transformation. Commonly used plant selectable markers include the hygromycin phosphotransferase ("hpt") gene, the phosphinothricin acetyl transferase gene ("bar"), the 5-enolpyruvylshikimate-3-phosphate synthase ("EPSPS"), neomycin 3'-O-phosphotransferase ("npt II"), or acetolactate synthase ("ALS").

The plasmid preferably also includes suitable promoters for expression of the nucleic acid encoding the antimicrobial polypeptide and for expression of the marker gene. The cauliflower mosaic virus 35S ("CaMV-35S") promoter is commonly used for plant transformation. For example, in plasmid pCEA1 used in the following examples, both the nucleic acid molecule encoding an antimicrobial polypeptide and the marker gene are under the control of the CaMV 35S promoter. Other promoters useful for plant transformation include WIN, NOS, MAS, TR, PIN, rbc S-E9, 2019E, TobRB7, and the like.

For plant transformation, the plasmid also preferably includes a nucleic acid molecule encoding a 3' terminator such as that from the 3'non-coding region of genes encoding a proteinase inhibitor, actin, or nopaline synthase ("NOS").

Other suitable plasmids for use in the subject invention can be constructed. For example, genes encoding antimicrobial polypeptides other than the ESF12 gene could be ligated into plasmid pCEA1 after use of restriction enzymes to remove the ESF12 gene. Other promoters could replace the CaMV 35S gene promoter present in pCEA1. Alternatively, other plasmids in general containing antimicrobial polypeptide genes under the control of a suitable promoter, with suitable selectable markers, can be readily constructed using techniques well known in the art.

Having identified and constructed the plasmid, one technique of transforming plant cells with a nucleic acid molecule which encodes the antimicrobial polypeptide is by contacting the plant cell with an inoculum of a bacteria previously transformed with the plasmid. Generally, this procedure involves inoculating the plant cells with a suspension of a transformed bacteria (e.g. *A. tumefaciens*) and incubating the cells for 48 to 72 hours on regeneration medium without antibiotics at 25°–28° C.

Bacteria from the genus Agrobacterium can be utilized to transform plant cells. Suitable species include *Agrobacterium tumefaciens* and *Agrobacterium rhizogenes*. *Agrobacterium tumefaciens* (e.g., strains LBA4404 or EHA105) is particularly useful due to its well-known ability to transform plants.

In inoculating the cells of plants with Agrobacterium according to the subject invention, the bacteria must be transformed with a vector which includes a nucleic acid molecule encoding for an antimicrobial polypeptide.

Plasmids, suitable for incorporation in Agrobacterium, which include a nucleic acid molecule encoding for an antimicrobial polypeptide, generally contain an origin of replication for replication in the bacterium *Escherichia coli*, an origin of replication for replication in the bacterium *Agrobacterium tumefaciens*, T-DNA right border sequences for transfer of genes to plants, and marker genes for selection of transformed plant cells. Particularly preferred is the vector pBI121 which contains a low-copy RK2 origin of replication, the neomycin phosphotransferase ("nptII") marker gene with a nopaline synthase ("NOS") promoter and a NOS 3' polyadenylation signal. T-DNA plasmid vector pBI121 is available from Clonetech Laboratories, Inc., 4030 Fabian Way, Palo Alto, Calif. 94303. A nucleic acid molecule encoding for an antimicrobial polypeptide is inserted into the vector to replace the beta-glucuronidase ("GUS") gene (for example, as in the plasmid pCEA1).

Typically, Agrobacterium spp. are transformed with a plasmid by direct uptake of plasmid DNA after chemical and heat treatment, as described by Holsters et al. (1978); by direct uptake of plasmid DNA after electroporation, as described by Shen and Forde (1989); by triparental conjugational transfer of plasmids from *Escherichia coli* to Agrobacterium mediated by a Tra+ helper strain as described by Ditta et al. (1981); or by direct conjugational transfer from *Escherichia coli* to Agrobacterium as described by Simon et al. (1982).

Another method for introduction of a plasmid containing nucleic acid encoding an antimicrobial peptide into a plant cell is by transformation of the plant cell nucleus, such as by particle bombardment. As used throughout this application, particle bombardment (also know as biolistic transformation) of the host cell can be accomplished in one of several ways. The first involves propelling inert or biologically active particles at cells. This technique is disclosed in U.S. Pat. Nos. 4,945,050, 5,036,006, and 5,100,792, all to Sanford et al., which are hereby incorporated by reference. Generally, this procedure involves propelling inert or biologically active particles at the cells under conditions effective to penetrate the outer surface of the cell and to be incorporated within the interior thereof. When inert particles are utilized, the plasmid can be introduced into the cell by coating the particles with the plasmid containing the heterologous DNA. Alternatively, the target cell can be surrounded by the plasmid so that the plasmid is carried into the cell by the wake of the particle. Biologically active particles (e.g., dried bacterial cells containing the plasmid and heterologous DNA) can also be propelled into plant cells. This method can also be used to introduce linear DNA molecules encoding an antimicrobial polypeptide into a plant cell.

A further method for introduction of the plasmid into a plant cell is by transformation of plant cell protoplasts. Plant protoplasts are enclosed only by a plasma membrane and will therefore take up macromolecules like heterologous DNA. These engineered protoplasts can be capable of regenerating whole plants. Suitable methods for introducing heterologous DNA into plant cell protoplasts include electroporation and polyethylene glycol ("PEG") transformation. As used throughout this application, electroporation is a transformation method in which, generally, a high concentration of plasmid DNA (containing heterologous DNA) is added to a suspension of host cell protoplasts and the mixture shocked with an electrical field of 200 to 600 V/cm. Following electroporation, transformed cells are identified by growth on appropriate medium containing a selective agent.

As used throughout this application, transformation encompasses stable transformation in which the plasmid is integrated into the plant chromosomes.

Other methods of transformation can also be used to successfully transform plants, including the protoplast method (for a review, see Cao et al. 1992), and the Agrobacterium method (Hiei et al. 1994). Biolistic transformation has been used to successfully transform maize (for a review, see Mackey et al. 1993) and wheat (see U.S. Pat. No. 5,405,765 to Vasil et al.).

Once a plant cell or protoplast is transformed in accordance with the present invention, it is regenerated to form a transgenic plant. Generally, regeneration is accomplished by culturing transformed cells or protoplasts on medium containing the appropriate growth regulators and nutrients to allow for the initiation of shoot meristems. Appropriate antibiotics are added to the regeneration medium to inhibit the growth of Agrobacterium or other contaminants and to select for the development of transformed cells or protoplasts. Following shoot initiation, shoots are allowed to develop in tissue culture and are screened for marker gene activity.

In suitable transformation methods, the plant cell to be transformed can be in vitro or in vivo, i.e. the plant cell can be located in a plant.

The invention also provides a transgenic plant produced by the method of the subject invention, as well as seed produced by the transgenic plant.

The invention further provides a plant cell or protoplast or a transgenic plant transformed with a nucleic acid encoding an antimicrobial peptide that confers resistance to the microbe in the plant generated from the plant cell or protoplast or in the transgenic plant. As discussed above, various plants and genes encoding an antimicrobial polypeptide can be utilized.

Preferably, the nucleic acid encoding an antimicrobial polypeptide is controlled by a strong promoter to effect maximum expression of the antimicrobial polypeptide, or by a stress-induced promoter to effect induction of the promoter in response to stress conditions. In one embodiment, the transgenic plant cell or protoplast or plant is transformed with the nucleic acid encoding the promoter, such as the CaMV 35S promoter, by providing a plasmid which includes DNA encoding the antimicrobial polypeptide and the promoter.

Since pathogens normally attack cells, and in particular plant tissue, from locations outside the cell, it may be desirable for the antimicrobial polypeptides of the subject invention to be secreted from the transformed plant cell. This may be accomplished by appending a peptide sequence, known in the literature as a signal sequence or as a leader sequence, to effect secretion of the polypeptide from the cell. Suitable signal sequences include Pr-1a, Pr-1b, and Pr-1c leaders from tobacco (Pfitzner and Goodman 1987), sCEC leader from the insect *Hyalophora ceropia* (Denecke et al. 1990), and the ap24 leader from tobacco (Melchers et al. 1993).

In cases where constitutive expression of the polypeptides is not necessary for protection against pathogens, it is advantageous to confine expression of the antimicrobial peptides to the tissues most susceptible to pathogen attack. This can be accomplished by using suitable targeting promoters, such as wound inducible promoters. Preferable wound-inducible promoters suitable for use in the present invention are win 3.12 (Hollick and Gordon 1993) and win 6.39B (Davis et al. 1991). Construction of vectors containing the wound-inducible promoters, such as pWEA1 and pWEA2, can be achieved using standard subcloning techniques (Sambrook et al. 1989) to insert these promoters into the pCEA1 plasmid to control expression of the nucleic acid molecules encoding antimicrobial polypeptides. Signal sequences can also be used to target expression of the antimicrobial polypeptides to specific plant organelles.

Many plant signal or leader sequences are known in the art. These include those from Genbank Accession Nos.: ABU44127, ECU47048, PLLEP0, GBDA3SL, GBDB5SL, MIU09180, PDHEMOG, PMNSLRNA, PMNSLRNB, PMNSLRNC, PMNSLRND, CHEGZ, CHSARRN1, CRU12573, DCSBFRU, GMAC6L, GMAC7L, GMHSF34, GMTEFS1, HVADH2, HVADH3, HVB193G, HVB914, LEBFRUCG, LPBFRUCG, RCCSCP, RCCSCPS, SALCPRG, SOPSAD, SORBCS1, SOSFAD6, STU02608, STU14SNR, TOBP20PR, U01901, ZMBPERU, ZMBPERUM, ZMNRNA512, ZMU14SNR, ZMU14SNRA, ZMU14SNRB, ZMU14SNRC, ZMU14SNRD, ZMU3SNRNG, SYNATS1A, MBSRNAL, MBSRNAN, MBSRNA0, MCVCP, SYECG, SYERNA, and SYETRAILER. As used herein, any discussion of the antimicrobial polypeptide of the subject invention is intended to include those embodiments in which one of these leader or signal sequences is attached to the polypeptide, whether it be attachment at the DNA level or expression at the polypeptide level.

The plant cell or protoplast or plant can also be transformed with a nucleic acid encoding a selectable marker, such as the bar gene, to allow for detection of transformants, and with a nucleic acid encoding the cauliflower mosaic virus 35S promoter to control expression of the nucleic acid molecule. Other selectable markers include genes encoding EPSPS, nptII, or ALS. Other promoters include those from genes encoding actin 1, ubiquitin, and PINII. These additional nucleic acid sequences can also be provided by the plasmid encoding the antimicrobial peptide and its promoter. Where appropriate, the various nucleic acids could also be provided by transformation with multiple plasmids.

Plant breeders, geneticists, and pathologists have been combating pathogens for more than a century and have produced many hundreds of disease-resistant varieties. In many cases, within a few years to a few decades of commercial release, the resistant variety is successfully attacked by a new strain of the pathogen. The length of time a variety retains its resistance is called "durability". Many variables affect durability, but one of the most frequently cited causes of low durability is resistance based on a single gene product. This problem is potentially even more pronounced in woody perennials than with annual crops because individual plants are exposed to a pathogen population for years to decades. This long-term exposure enhances the probability of selecting pathogens that can overcome the single-gene resistance. Antimicrobial peptides are the simplest of single-gene traits. Therefore, it is possible that pathogens could evolve quickly to overcome resistance based on a single antimicrobial peptide.

To genetically engineer durable resistance, a multi-layered defense system could be employed using two or more gene-products, each utilizing a different inhibitory mechanism. A single mutation overcoming the effects of just one antimicrobial peptide would have no selective advantage because the plant's other peptide would prevent propagation of the mutated pathogen. For a pathogen to overcome two or more different antimicrobial peptides would require multiple mutations to simultaneously overcome the effects of each. It is highly improbable that such multiple mutations would simultaneously occur in a single microorganism. The probability decreases with each additional antagonistic gene product. Therefore, a genetic engineering strategy utilizing several antimicrobial gene products should produce highly durable resistance.

For example, the gene constructs can be designed to express multiple gene products from a single gene construct under the control of a single promoter. This option has the advantage of linking the coding regions, keeping the gene construct small, and minimizing the transformation procedures. This method takes advantage of a second initiation in translation. If two open reading frames ("ORFs") are located within a few base pairs of one another, and the first ORF is small, the second ORF can also be expressed, though at a reduced rate (Putterill and Gardner 1989). In one particularly useful gene construct, the two ORFs encoding two antimicrobial peptides are next to one another and contain efficient translational initiation sites.

The invention is also directed to a transgenic plant regenerated from the transgenic plant cells or protoplasts, as well as to seed produced by the transgenic plants. The invention is also directed to seed, which upon germination, produces the transgenic plant.

While the nucleotide sequence referred to herein encodes an antimicrobial polypeptide, nucleotide identity to a nucleotide sequence identified herein is not required. As should be readily apparent to those skilled in the art, various nucleotide substitutions are possible which are silent mutations (i.e. the amino acid encoded by the particular codon does not change). It is also possible to substitute a nucleotide which alters the amino acid encoded by a particular codon, where the amino acid substituted is a conservative substitution (i.e. amino acid "homology"is conserved). It is also possible to have minor nucleotide and/or amino acid additions, deletions, and/or substitutions in the antimicrobial polypeptide nucleotide and/or amino acid sequences which have minimal influence on the properties, secondary structure, and hydrophilic/hydrophobic nature of the encoded antimicrobial polypeptide. These variants are encompassed by the nucleic acid encoding an antimicrobial polypeptide according to the subject invention.

Non-essential nucleotides could be placed at the 5' and/or 3' end of the antimicrobial peptide without affecting the functional properties of the molecule (i.e. in increasing microbial resistance). For example, the nucleotides encoding the peptide may be conjugated to a signal (or leader) sequence at the N-terminal end (for example) of the peptide which co-translationally or post-translationally directs transfer of the peptide. The nucleotide sequence may also be altered so that the encoded peptide is conjugated to a linker or other sequence for ease of synthesis, purification, or identification of the peptide.

The following examples are offered by way of illustration, not limitation, of the present invention.

MATERIALS AND METHODS

Peptide Design

All peptides were designed so that they had an α-helical conformation as predicted by the Chou-Fasman (Chou and Fasman 1978 and Chou 1990) or Garnier-Robson (Garnier et al. 1978) algorithms. The presence of an amphipathic region was predicted by the Eisenberg Moment (Eisenberg et al. 1984). The PROTEAN program from DNASTAR, Inc. (Madison, Wis.) was employed for these analyses.

Peptide Synthesis

Six antimicrobial polypeptides, designated ESF1 (SEQ ID NO:3), ESFLB (SEQ ID NO:7), ESF5 (SEQ ID NO:10), ESF6 (SEQ ID NO:13), ESF12 (SEQ ID NO:1), ESF17 (SEQ ID NO:4), and ESF15 (SEQ ID NO:14) were designed in accordance with the above considerations. Two other ESF peptides, ESF4 and ESF13, contained uncharged polar and negative amino acid substitutions for the positive amino acids in the ESF1 sequence, respectively (see Powell et al. 1995). These were used to test the necessity of the positive charges. All sequences were synthesized and purified to greater than 80% purity by Genosys Biotechnologies (The Woodlands, Tex.). Magainin II, (Ala$^{8,13,18}$)Magainin II amide, and cecropin B (HPLC purified to 97%) were purchased from Sigma (St. Louis, Mo.).

Fungal Strains, Bacterial Strains, and Pollen Collections

*Cryphonectria parasitica*, strain EP42, was obtained from American Type Culture Collection, Rockville, Md. (ATCC Accession No. 38751). *Fusarium oxysporum* f. sp. lycopersici, strain 73 was obtained from Felice Cervone, Plant Biology Department, University of Rome, Italy. The cultures were maintained on potato dextrose agar supplemented with methionine and biotin, PDAmb (Anagnostakis 1982). *Septoria musiva*, strain 92–49C, was obtained from Glen Stanoz, University of Wisconsin, Madison, Wis.

Three bacteria were assayed. *Agrobacterium tumefaciens*, wild-type strain Bo542 (Sciaky et al. 1978) was provided by Eugene Nester, Washington State University, Seattle, Wis. Erwinia amylovora (Collection 88–100, highly virulent on cherry) and *Pseudomonas syringae* (Collection PSS34, streptomycin resistant) were provided by Thomas Burr, Department of Horticultural Sciences, Cornell University, New York State Agricultural Experiment Station, Geneva, N.Y. Stock cultures of *P. syringae* and *E. amylovora* were maintained on King's Medium B Agar (KB, Atlas and Parks 1993). *A. tumefaciens* was maintained on potato dextrose agar ("PDA").

Pollen collections for Chinese chestnut (*Castanea mollissima*), tomato (*Lycopersicon esculentum*), and willow (*Salix lucida*) clone 507 were made in central New York. Chestnut catkins and tomato flowers were placed into paper bags in an ice chest. Within 2 hr after collection, catkins were cut into 1.0 cm segments and tomato anthers were placed into sterile 15 ml Falcon tubes. The tubes were "capped" with parafilm punctured with 12–15 holes and lyophilized for 24 hr. Lyophilized samples were stored at −20°C. until removed for rehydration.

Willow pollen was extracted using the protocol described by de Niella and Maynard (1993). Catkins were gently stirred in carbon tetrachloride. The pollen/carbon tetrachloride suspension was filtered (Whatman filter paper) with suction. The pollen was transferred to microfuge tubes (1.5 ml) with a fine-bristle artist's brush and stored at −20° C.

Apple (*Malus domestica*) cultivar "Empire" pollen was supplied by Susan Brown, Department of Horticultural Sciences, Cornell University, New York State Agricultural Experiment Station, Geneva, N.Y.

To rehydrate, small amounts of pollen were placed in open microfuge tubes (1.5 ml) which were placed into a closed glass petri dish with a dampened tissue. Pollen was rehydrated overnight in a dark chamber at 14° C.

Determination of the Minimal Inhibitory Concentration

Dilutions of peptides, prepared in sterile deionized water, were placed (20 µl aliquots) in Corning disposable sterile polystyrene ELISA plates (96 well, high binding) which had been pretreated with bovine serum albumin by rinsing each well with 200 µl of a 1.0 mg/ml solution.

Media (PDAmb, pH 5.2) was prepared with deionized water, Difco potato dextrose broth (12 g/L), Sigma D,L-methionine (0.05 g/L), Sigma biotin (2 mg/L), and Fisher-Biotech low melting point agarose (20 g/L). Sterilized media was added to the wells to make a final volume of 100 µl and allowed to harden for 3 hr prior to inoculation with 10 µl of conidial suspension. Peptide concentrations tested were 0, 1.25, 2.5, 5, 10, 15, 20, 25, 50, 100, 150, 200, and 250 µM.

Fungal conidial suspensions were aseptically prepared from agar plate cultures of *C. parasitica* and *S. musiva* or liquid cultures for *F. oxysporum* f.sp. lycopersici. Conidia were suspended from agar plates with 10 ml sterile 1% Tween 20. All culture suspensions were filtered through four layers of sterile cheesecloth, collected in sterile 15 ml Falcon tubes, and centrifuged for 3 min at 1900×g. The pellets were then suspended in 10 ml sterile deionized water and centrifuged for 3 min at 1900×g. The "washed" pellets were suspended in 5 ml sterile deionized water. The conidial concentration was determined using a hemocytometer (Fisher ultra plane, Neubauer ruling) and then diluted to $1.0 \times 10^4$ conidia/ml.

Approximately 100 conidia (10 µl) were transferred to each microtitre plate well. Microtitre plates were incubated in ambient light at room temperature in a moist chamber (plastic box containing wet paper towels and covered with clear plastic wrap). Tests with *S. musiva* used continuous light. Plates were scored for growth at 6 days and photographed. All tests were repeated 4 or more times. Controls without peptides were included with all tests. The Minimum Inhibitory Concentration ("MIC") of the fungal conidia was the lowest peptide concentration which totally prevented germination on the medium in all the repeated tests.

Bacterial suspensions of *A. tumefaciens, E. amylovora,* and *P. syringae* were obtained from liquid cultures grown in Luria Broth (Atlas and Parks 1993). Cultures were grown at 25°C. on a rotary shaker (110 rpm) for 14 hr. Bacterial cell suspensions with an optical density between 0.7 and 0.85 at 600 nanometers ($OD_{600}$) were used for assay inoculations. Dilutions of peptides were placed in the 96-well ELISA plates as described above. The final peptide concentrations tested were 0, 0.625, 1.25, 2.5, 5, 10, 15, 20, 25, 50, 100, and 250 μM. All tests were repeated 2 or more times. Controls without peptides were included with all tests. The MIC for bacterial cells was the lowest peptide concentration associated with no visible bacterial lawn or isolated colonies on the medium after 3 days in all the repeated tests.

Rehydrated plant pollen was diluted with sucrose-boric acid medium ("SBM") to a concentration of 80 grains/μl (Neubauer hemocytometer). Media for pollen germination (SBM, pH 6.2) was prepared with deionized distilled water, sucrose (150 g/L), and boric acid (150 mg/L). Dilutions of all peptides tested against rehydrated pollen grains were aseptically prepared with sterile SBM. Aliquots (50 μl) of peptide solutions were aseptically placed in ELISA microtitre plates as before. Approximately 400 pollen grains (5 μl) were added to the 50 μl volume of peptide solution in the well to give the final peptide concentrations of 0, 1.25, 2.5, 5, 10, 15, 20, 25, 50, 100, 150, 200, and 250 μM. Microtitre plates were incubated in the dark at room temperature for 24 hr. Germination of pollen grains was observed with Zeiss stereo dissecting scope (Schott cold light source) and photographed. The MIC of the plant pollen was the lowest concentration that totally inhibited germination in the medium. All tests were repeated 4 or more times. Controls without peptides were included with all tests. The highest concentration tested was 250 μM. If germination occurred at this concentration, the MIC is yet undetermined, but it is known to be greater than 250 μM.

Trypsin, Proteinase K, and HCl Treatments of ESF12

A solution containing 1250 μM ESF12 and 1000 Units trypsin was incubated at 37° C. for 30 minutes. Another solution containing 1250 μM ESF12 and 2.5 μg of proteinase K was incubated at 37° C. for 30 minutes. Solutions (250 μl) containing only sterile deionized water, 500 units of trypsin, and 1.25 μg proteinase K (all incubated at 37° C. for 30 min) were used as controls. The two treated ESF12 peptide solutions were assayed at 2.5, 5, 10, 20, 25, 50, 100, 250 μM final concentrations. The medium for fungal growth was PDAmb. Conidial suspensions of *F. oxysporum* f.sp. lycopersici were prepared and MICs tested as before.

A solution containing 2500 μM ESF12 and 10 mM HCl was incubated at 37° C. for 30 minutes and then neutralized with an equal volume of sterile 10 mM KOH. Peptide dilutions (2.5, 5, 10, 20, 25, 50, 100, and 250μM) were aseptically prepared from this neutralized solution for assay with *F. oxysporum* f.sp. lycopersici as before. Neutralized 10 mM HCl and sterile deionized distilled water were the controls.

Gene Design and Synthesis

The ESF12 peptide design was chosen to test the ability of the ESF peptides to confer increased pathogen resistance. Since no natural source of ESF12 exists, a gene capable of expressing it in a transgenic plant had to be designed and then constructed. Several considerations were taken into account to assure design flaws would not interfere with optimal expression. Because of redundancy in the genetic code, 1–6 codons may specify the same amino acid. For example, six different codons specify arginine but only one specifies methionine. Although the genetic code is common among all eukaryotes, there are differences in frequency of use among distantly related organisms. Since these gene constructs were going to be tested in tree species, codons encoding the ESF12 and Ac-AMP1.2 polypeptides (Ac-AMP1.2 is another antimicrobial peptide; see Broekaert et al. 1992) were chosen from a set of 44 dicot-"preferred" codons (Campbell and Gowri 1990).

Referring to FIG. 1, the plasmid pCEA1 was constructed by digesting the parent plasmid pBI121 (CLONETECH) with the restriction enzymes BamHI and SstI. This digestion removes the Gus gene. A nucleic acid construct (SEQ ID NO:21) was synthesized which includes: a) a 5' nontranslated portion which includes BamHI, SalI, SspI and XhoI unique restriction sites, provided for ready manipulation of the construct into various plasmids; b) a KOZAK recognition sequence; c) nucleotides encoding the ESF12 antimicrobial polypeptide, namely, nucleotides 34–87 of SEQ ID NO:21; the ATG start codon at nucleotides 34–36 of SEQ ID NO:21 encodes the N-terminal methionine of the ESF12 antimicrobial polypeptide; d) a TAA stop codon at nucleotides 88–90 of SEQ ID NO:21; e) an NcoI unique restriction site separating the ESF12 coding region from the AcAMP1.2 coding region, in the event that it is desirable to remove either coding region, as part of a second KOZAK recognition sequence; f) nucleotides encoding the AcAMP1.2 antimicrobial peptide (Broekaert et al. 1992), namely nucleotides 93–179 of SEQ ID NO:21, which encode the AcAMP1.2 peptide having an amino acid sequence as shown in SEQ ID NO:22; the ATG start codon at nucleotides 93–95 of SEQ ID NO:21 encodes the N-terminal methionine of the AcAMP1.2 antimicrobial peptide; g) a TAA stop codon at nucleotides 180–182 of SEQ ID NO:21; and h) SacI and SstI unique restriction sites at the 3' end of the construct. This construct (SEQ ID NO:21) was digested with BamHI and SstI to obtain sticky ends, and the digested pBI121 plasmid was mixed with the digested construct, and ligated with T4 DNA ligase, to generate the plasmid pCEA1. The plasmid pCEA1 was then used to perform transformations of plants (see below).

The plasmid pCEA1 is merely an example of a suitable plasmid for use in the subject invention. Standard cloning techniques could be used to insert a nucleic acid molecule encoding the antimicrobial polypeptide (ESF12, or others, or a combination thereof) into any of the various known plant vectors. Furthermore, variations of the pCEA1 vector can readily be constructed. If a different promoter is desired, the CaMV 35S promoter can be removed by cutting the pCEA1 vector with the restriction enzymes HindIII and BamHI, and replacing the CaMV 35S promoter sequence with the desired promoter sequence. It is also possible to insert a different promoter downstream from the CaMV 35S promoter, but upstream of the ESF12 coding region, in order to drive expression of the ESF12 polypeptide with the different promoter. For example, the plasmid pWEA1 was constructed by cutting the pCEA1 plasmid with the restriction enzymes BamHI and XhoI, and inserting the win 3.12 promoter into the 5' non-coding region of the ESF12 construct (into SEQ ID NO:21). The win 3.12 promoter is upstream of the ESF12 coding region and drives expression of the ESF12 gene. The plasmid pWEA2 was constructed by cutting the pCEA1 plasmid with the restriction enzymes SalI and XhoI and inserting the win 6.39B promoter, again upstream of the ESF12 coding region. The particular plasmids disclosed herein are thus examplary of the plasmids which can be used in the subject invention, and can be readily manipulated and altered using known techniques to construct variations of the disclosed plasmids.

Referring again to the ESF12 construct (SEQ ID NO:21), each open reading frame ("ORF") includes an efficient translation initiation site. In most plant mRNA, the 5' proximal AUG is the initiation codon (Joshi 1987) but initiation is also determined by the context of the AUG (Kozak 1986b). The animal initiation consensus sequence (CCACCAUGG) and the plant initiation consensus sequence have been shown to initiate translation equally well in tobacco mesophyll cells (Guerineau et al. 1992). The animal consensus sequence has the advantage of containing a NcoI restriction endonuclease recognition site (CCATGG) in the genes DNA sequence. The location of this restriction site can be used in future modifications, such as the addition of leader sequences which target the gene product to various parts of the cell.

Next, a termination codon was chosen. In dicots, the mRNA termination codon UAA is preferred (46%) over UGA (36%) or UAG (18%) (Angenon et al. 1990). Data suggested that efficient termination in plants might require a tetranucleotide sequence of UAAA, UGAA, or UAGA where A is preferred (41%) and C is avoided (6%) in the last position (Angenon et al. 1990). Since plants contain tRNAs capable of misreading UAG, the UAGA sequence was used to prevent this stop codon from being "leaky" and producing an undesirable oversized product.

Lastly, the resulting nucleotide sequences were tested using computer modeling and modified to produce minimal mRNA secondary structure. Folding of mRNA into hairpin loops or other secondary structures can inhibit translation (Kozak 1986a). Minimizing secondary structures also aids the synthesis of the DNA used to produce the gene construct. The resulting DNA sequence (SEQ ID NO:21) was then synthesized and cloned into the plant binary vector pBI121 (CLONETECH Laboratories, Inc., Palo Alto, Calif.), replacing the GUS gene, to form plasmid pCEA1 (see FIG. 1).

Promoter Evaluation

To ensure proper expression of the gene construct, several promoters were tested. First the constitutive CaMV 35S promoter was used in the vector pCEA1 (FIG. 1). The CaMV 35S promoter is considered to be a strong constitutive promoter and was used primarily to determine the effects on the plant tissues of expressing the peptides. If high concentrations of the peptides damage or kill plant cells, a complete inability to regenerate transformants would be expected. If the gene were sub-lethal, but still toxic, observation of severely altered phenotypes among the transgenics would be expected. Putative transformants of poplar were obtained.

It is unlikely that constitutive expression of the peptides would be necessary for protection against pathogens. Therefore, a set of wound-inducible promoters that should confine expression of the antimicrobial peptides to the tissues most susceptible to pathogen attack was examined. The wound-inducible promoters evaluated were win3.12 (Hollick and Gordon 1993) and win6.39b (Davis et al. 1991). Vectors pWEA1 and pWEA2, containing the wound-inducible promoters, were constructed using standard subcloning techniques (Sambrook et al. 1989) from the pCEA1 parent plasmid.

EXAMPLE I

In Vitro Characterization of Antimicrobial Polypeptides

Table 1 compares the MIC of selected magainins, cecropins, and ESF peptides (antimicrobial polypeptides) as tested against fungal conidia, plant pathogenic bacteria, and plant pollen.

EXAMPLE II

Transformation of the Hybrid Clone "Ogy"

The plasmid pCEA1 was cloned into the Agrobacterium strain LBA 4404 by triparental mating and then used to transform poplar employing the leaf-piece transformation method described in Horsch et al. (1985). Leaf and stem explants were cut into pieces approximately 1 to 2 cm in size, transferred to liquid stage I medium (Table 2), and inoculated with Agrobacterium containing the pCEA1 vector. After 48 to 72 hours of cocultivation, the explants were transferred to a stage I agar medium containing the antibiotics carbenicillin (200 μg/ml) and cefotaxime (100 μg/ml) to kill the Agrobacterium cells. After approximately one week, the explants were transferred to fresh medium containing carbenicillin, cefotaxime, and geneticin (25 μg/ml). (Geneticin is growth inhibitory or toxic to normal plant cells, but only mildly inhibitory to cells that have been transformed by the Agrobacterium vector containing an active nptII gene.) Once shoots developed, they were transferred to stage II medium (Table 3) containing carbenicillin, cefotaxime, and geneticin. The developing shoots were transferred every two to four weeks to fresh selective medium for several months until any shoots developing on the non-transformed controls were dead.

Transformation of the poplar was then confirmed by extracting DNA from regenerated plantlets and amplifying the gene construct using the polymerase chain reaction ("PCR") (Kit from Perkin-Elmer Corp., Norwalk, Conn.) with primers specific for ESF12 gene sequences.

To confirm translation of ESF12, partially purified peptides are isolated from the tissues of selected transformants. The level of peptide expression is tested using standard ELISA techniques (Crowther 1995) using ESF12 antibodies produced by conventional techniques, such as those described in Coico (1995).

EXAMPLE III

Genetic Transformation of American Chestnut

*Agrobacterium tumefaciens* strains LBA 4404 containing the pCEA1 vector (containing nucleic acid encoding ESF12) and LBA 4404 containing the pCGN7314 vector (control), and single-node stem segments (3 mm long) of American chestnut clones "B'ville" and "Iowa #2", were used in Agrobacterium-mediated transformation studies. Plasmid pCEA1 (target) and pBI121 (control) and embryogenic calli of American chestnut derived from immature ovules of clones "Pond" and "Wishing Well" were used in particle-bombardment mediated transformation studies.

The media used in genetic transformation are listed in Table 4. Antibiotics (geneticin and carbenicillin) were filter sterilized and added to autoclaved media when it had cooled to approximately 48° C. Unless otherwise mentioned, the cultures were maintained at 23° (±2) °C. on benches illuminated 16 hours daily with cool white fluorescent light (30 μM m$^{-2}$ s$^{-1}$)

Agrobacterium-mediated transformation was conducted as set forth below.

Stem segments were pre-cultivated on a shoot-multiplication medium for 24 hours. Precultivated explants were then inoculated with overnight-grown cultures of *A. tumefaciens* for 30 minutes, followed by cultivation on the shoot-multiplication medium for 48 hours. The co-cultivated explants were washed with selective medium 1 without phytagel and cultivated subsequently on selective medium 1 until shoots grew out. During this period, explants were subcultured biweekly by cutting surviving segments to small pieces (approximately 3×3×'mm) and transferring to fresh selective medium. The callus-bud masses were then cultivated on the selective medium 2 until survival shoots were approximately 2 cm tall.

Whole plants were then regenerated and acclimated. Surviving shoots (approximately 2 cm tall) were excised from shoot-callus masses and wounded by splitting their base vertically through the pith, approximately 2 mm up the stem. Each cutting was then soaked in 5 mM IBA (for clone "B'ville") or 10 mM IBA (for clone "Iowa #2") for 1 min, inserted vertically approximately one-fourth of their total length into rooting medium, and cultivated for 2 weeks.

The mature embryos were cultivated on embryo maturation medium until plantlets were 3 to 5 cm tall, and acclimatized in a potting mix (1:1 moss peat:sand).

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

MIC (in $\mu$M) of Natural and Synthetic Antimicrobial Polypeptides

|  | Magainin I | Magainin II | Cecropin B | ESF1 | Ala$^{8,13,15}$ ESF1B | ESF4 | ESF5 | ESF6 | ESF12 | ESF13 | ESF15 | ESF17 |
|---|---|---|---|---|---|---|---|---|---|---|---|---|
| Fungi |  |  |  |  |  |  |  |  |  |  |  |  |
| Septoria musiva | 5 | 10 | 5 | 5 | — | >250 | 5 | 5 | 2.5 | >250 | — | 250 |
| Fusarium oxysporum | 15 | 15 | 20 | 2.5 | 1.25 | >250 | 5 | 10 | 20 | >250 | 25 | 250 |
| Cryphonectria parasitica | 10 | 30 | 15 | 2.5 | — | >250 | 10 | 10 | 10 | >250 | — | 100 |
| Bacteria |  |  |  |  |  |  |  |  |  |  |  |  |
| Agrobacterium tumefaciens | — | 100 | — | — | — | — | — | — | 50 | — | — | — |
| Erwinia amylovora | — | 250 | — | — | — | — | — | — | 250 | — | — | — |
| Pseudomonas syringae | — | 250 | — | — | — | — | — | — | 250 | — | — | — |
| Plants |  |  |  |  |  |  |  |  |  |  |  |  |
| Salix lucida | — | — | — | >250 | — | >250 | >250 | >250 | >250 | >250 | — | — |
| Castanea mollissima | — | — | — | >250 | — | >250 | >250 | >250 | >250 | >250 | — | — |
| Malus domestica | — | — | — | — | — | — | — | — | >250 | — | — | — |
| Lycopersicon esculentum | — | — | — | — | — | — | — | — | >250 | — | — | — |

After roots were initiated, microcuttings were transferred back into shoot-elongation media and cultivated for 3 weeks. Rooted plants were then cultivated on growth regulator-free MS medium until they were 3 to 5 cm tall. Finally, plants were acclimatized in a potting mix consisting of a one-to-one mixture of peat moss and sand.

Particle bombardment-mediated transformation was effected as follows.

Small pieces (approximately 3×3×3 mm) of embryogenic calli were pre-cultivated on embryo initiation medium in darkness for 24 hours. 1.1 $\mu$m tungsten particles were coated with either pBI121 or pCEA1. The embryogenic calli were then bombarded with the coated tungsten particles using a BIOLISTIC™ PDS-1000/He device. The helium pressure was about 1300 psi, and the distance between the rupture disk and the macrocarrier was about 1 cm. The macrocarrier flight distance was about 1.1 cm, and the microcarrier flight distance was about 9 cm.

The bombarded calli were cultivated on embryo initiation medium in darkness for 5 days and then selectivly cultivated on selective medium 3 for 2 months in the darkness. During selective cultivation, the explants were subcultured biweekly by cutting surviving calli to small pieces (approximately 3×3×3 mm) and transferring the small pieces to the fresh selective medium. The surviving callus-embryo masses were then cultivated on selective medium 4 under 16-hour photoperiod for 4 weeks and then on selective medium 5 until the embryos were mature.

TABLE 2

Stage I medium (pH 5.0 for liquid, pH 5.7 for agar)

| Ingredient | per liter |
|---|---|
| MS salts, min. organics | 4.3 g |
| Nitsch & Nitsch vitamins | 0.109 g |
| sucrose | 30 g |
| BAP (1 mM stock solution) | 1.75 ml |
| NAA (1 mM stock solution) | 1.0 ml |
| CaCl$_2$ | 2.2 g |
| (if agar medium) | 7.0 g of agar |

TABLE 3

Stage II medium (pH 5.7)

| Ingredient | per liter |
|---|---|
| MS salts, min. organics | 4.3 g |
| Nitsch & Nitsch vitamins | 0.109 g |
| sucrose | 30 g |
| BAP (1 mM stock solution) | 0.5 ml |
| NAA (1 mM stock solution) | 1.0 ml |
| CaCl$_2$ | 2.2 g |
| agar | 7.0 g |

TABLE 4

Media for Genetic Transformation of American Chestnut

| Media | Components | Conc |
|---|---|---|
| Shoot-multiplication (pH5.5) | McCown's Woody Plant Medium salts | 1X |
| | Nitsch and Nitsch vitamins | 1X |
| | Sequestrene 330 Fe | 10 mM |
| | $CaCl_2$ | 6 mM |
| | $MgSO_4$ | 3 mM |
| | BA | 1 µM |
| | IBA | 0.5 µM |
| | Sucrose | 35 g/l |
| | Phytagel | 5 g/l |
| Shoot-elongation (pH5.5) | McCown's Woody Plant Medium salts | 1X |
| | Nitsch and Nitsch vitamins | 1X |
| | 2-[N-morpholino]ethanesulfonic acid | 500 mg/l |
| | polyvinylpyrrolidone (PVP 40) | 500 mg/l |
| | BA | 0.89 µM |
| | Sucrose | 30 g/l |
| | Phytagel | 3.5 g/l |
| Selective Medium 1 | Shoot-multiplication medium | 1X |
| | Geneticin | 50 µg/ml |
| | Carbenicillin | 500 µg/ml |
| Selective Medium 2 | Shoot-elongation medium | 1X |
| | Geneticin | 50 µg/ml |
| | Carbenicillin | 500 µg/ml |
| Rooting (pH5.5) | MS | 0.5X |
| | Charcoal (washed with HCl) | 2 g/l |
| | Sucrose | 20 g/l |
| | Phytagel | 3.5 g/l |
| Embryo Initiation (pH5.5) | McCown's Woody Plant Basal salts | 1X |
| | Nitsch & Nitsch vitamins | 1X |
| | casein (enzymatic hydrolysate) | 1 g/l |
| | 2,4-D | 4 mg/l |
| | BA | 0.25 mg/l |
| | sucrose | 30 g/l |
| | phytagel | 3.5 g/l |
| Embryo Maturation | Gamborg's B-5 basal medium | 1X |
| | BA | 1.1 mg/l |
| | NAA | 0.09 mg/l |
| | sucrose | 20 or 60 g/l |
| | phytagel | 3.5 g/l |
| Selective medium 3 | Embryo Initiation medium | 1X |
| | Geneticin | 50 µg/ml |
| Selective medium 4 | Embryo Maturation medium containing 20 g/l sucrose | 1X |
| | Geneticin | 50 µg/ml |
| Selective medium 5 | Embryo Maturation medium containing 60 g/l sucrose | 1X |
| | Geneticin | 50 µg/ml |
| Embryo Germination | MS Minimal Organic medium | 1X |
| | sucrose | 10 g/l |
| | phytagel | 5 g/l |

LIST OF REFERENCES CITED

Agerberth et al., *Eur. J. Biochem.*, 202:849–854 (1991).
Anagnostakis, S. L., *Mycologia*, 74:826–830 (1982).
Angenon, G. et al., *FEBS Letters*, 271:144–146 (1990).
Atlas, R. M. and Parks, L. C., *Microbiological Media.*, Boca Raton:CRC Press (1993).
Bevins, C. L. and Zasloff, M., *Annu. Rev. Biochem.* 59:395–414 (1990).
Blondelle, S. E. and Houghten, R. A., *Biochemistry*, 30:4671–4678 (1991).
Boman, H. G. et al., *FEBS Letters*, 259:103–106 (1989).
Bordo, D. and Argos, P., *J Mol Biol* 217:721–729 (1991).
Broekaert, W. F., et al., *Biochemistry*, 31:4308–4314 (1992).
Campbell, W. H. and Gowri, G., *Plant Physiol.*, 92:1–11 (1990).
Cao, J. et al., *Plant Cell Rep*, 11:586–591 (1992).
Chen, H.-C. et al., *FEBS Letters*, 236:462–466 (1988).
Chou, P. Y. and Fasman, G. D., *Adv. Enzymol.*, 47:45–148 (1978).
Chou, P. Y., *Prediction Of Protein Structure And The Principles Of Protein Conformation*, New York:Plenum Press, 549–586 (1990).
Christensen, B. et al., *Proc. Natl. Acad. Sci. USA*, 85:5072–5076 (1988).
Coico, R., ed, *Current Protocols in Immunology*, Vol. 1, New York: John Wiley & Sons, Inc., pp. 2.4.1–2.4.4 (1995).
Cornelissen, B. J. C. and Melchers, L. S., *Plant Physiol.*, 101:709–712 (1993).
Crowther, J. R., *Methods in Molecular Biology*, New Jersey:Humana Press, 42:223 (1995).
Davis, J. M. et al., *Plant Mol. Biol.*, 17:631–639 (1991). de Niella, P. R. and Maynard, C. A., "Storage of Chestnut and Willow Pollen," In: Mohn, C. A. (Complier) *Proceedings of the Second Northern Forest Genetics Association Conference*, Jul. 29–30, 1993, Roseville, Minn., St. Paul, Minn.:Northern Forest Genetics Association, Department of Forest Resources, University of Minnesota, pp. 171–180 (1993).
Denecke, J. et al., *Plant Cell*, 2:51–59 (1990).
Ditta, G. et al., *Proc. Natl. Acad. Sci. USA*, 77:7347–7351 (1981).
Eisenberg, D. et al., *Proc. Natl. Acad. Sci. USA*, 81(1):140–144 (1984).
French, S. and Robson, B., *J. Molecular Evolution* 19:171–175 (1983).
Galvin, S. B. and Schilperoort, R. A., eds., *Plant Molecular Biology Manual*, 2nd ed., Dordrecht, Netherlands:Kluwer Academic Press (1994).
Garnier, J. et al., *J. Mol. Biol.*, 120:97–120 (1978).
Gross, E. and Meinhofer, J., eds., *The Peptides: Analysis, Synthesis, Biology. Special Methods in Peptide Synthesis, Part A*, New York:Academic Press (1980).
Guerineau, F. et al., *Plant Mol. Biol.*, 18:815–818 (1992).
Hiei, Y. et al. *The Plant Journal*, 6:271–282 (1994).
Hollick, J. B. and Gordon, M. P., *Plant Mol. Biol.*, 22:561–572 (1993).
Holsters, M. et al., *Mol. Gen. Genet.*, 163:181–187 (1978).
Horsch, R. B. et al., *Science*, 227:1229–1231 (1985).
Joshi, C. P., *Nucleic Acids Res.*, 16:6643–6653 (1987).
Kozak, M., *Proc. Natl. Acad. Sci. USA*, 83:2850–2854 (1986a).
Kozak, M., *Cell*, 44:283–292 (1986b).
Mackey, C. J. et al., *Transgenic Plants*, 2:21–33 (1993).
Melchers, L. S. et al., *Plant Molecular Biology*, 21:583–593 (1993).
Pfitzner, U. M. and Goodman, H. M., *Nucleic Acids Res.*, 15:4449–4465 (1987).
Powell, W. A. et al., *Molecular Plant-Microbe Interactions*, 8:792–794 (1995).
Putterill, J. J. and Gardner, R. C., *Plant Science*, 62:199–205 (1989).
Sambrook et al., *Molecular Cloning: A Laboratory Manual*, 2d Edition, Cold Spring Harbor, N.Y.:Cold Spring Harbor Laboratory Press (1989).
Sciaky, D. et al., *Plasmid*, 1:238–253 (1978).
Shen, W. and Forde, B. G., *Nucleic Acids Res.*, 17:8385 (1989).
Simon, R. et al., *Biotechnology*, 1:784–791 (1982).
Soravia, E. et al., *FEBS Letters*, 228:337–340 (1988).
Studier et al., *Gene Expression Technology*, 185 (1990).
Taylor, W. R., *J. Theor. Biol.* 119:205–218 (1986).
Udenfriend, S. and Meinhofer, J., eds., *The Peptides: Analysis, Synthesis, Biology. Vol. 9: Special Methods in Peptide Synthesis, Part C*, San Diego:Academic Press (1987).
Wade, D. et al., *Biochemistry*, 87:4761–4765 (1990).
Zasloff, M., *Proc. Natl. Acad. Sci. USA*, 84:5449–5453 (1987).

What is claimed:

1. An isolated nucleic acid molecule encoding an antimicrobial polypeptide, wherein said nucleic acid molecule encodes an amino acid sequence as shown in a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, and SEQ ID NO:14.

2. An isolated nucleic acid molecule encoding a polypeptide, said polypeptide selected from the group consisting of:

a polypeptide comprising an amino acid sequence of 15+q amino acid residues, wherein residues number n, n+7, n+10, and n+14 are positively charged amino acids, wherein at least one of residues number n, n+7, n+10, and n+14 is arginine, wherein remaining amino acid residues are nonpolar amino acids or uncharged polar amino acids, wherein n is an integer from 1 to 1+q, and wherein q is 0, 1, 2, 3, 4, or 5;

a polypeptide comprising an amino acid sequence of 15+q amino acid residues, wherein residues number n, n+6, n+7, n+10, n+13, and n+14 are positively charged amino acids, wherein remaining amino acid residues are nonpolar amino acids or uncharged polar amino acids, and wherein n is an integer from 1 to 1+q, and wherein q is 0, 1, 2, 3, 4, or 5;

a polypeptide comprising an amino acid sequence of 15+q amino acid residues, wherein residues number n, n+7, and n+14 are positively charged amino acids, wherein remaining amino acid residues are nonpolar amino acids, wherein n is an integer from 1 to 1+q, and wherein q is 0, 1, 2, 3, 4, or 5; and a polypeptide comprising an amino acid sequence of 15+q amino acid residues, wherein residues number n, n+7, and n+10 are positively charged amino acids, wherein remaining amino acid residues are nonpolar amino acids, wherein n is an integer from 1 to 5+q, and wherein q is 0, 1, 2, 3, 4, or 5.

3. The isolated nucleic acid molecule of claim 1 or 2 wherein said nucleic acid is deoxyribonucleic acid.

4. The isolated nucleic acid molecule of claim 2 wherein the polypeptide has a methionine residue as an N-terminal amino acid.

5. The isolated nucleic acid molecule of claim 2 wherein the positively charged amino acids are the same or different and are selected from the group consisting of lysine, arginine, and histidine.

6. The isolated nucleic acid molecule of claim 2 wherein the nonpolar amino acids are the same or different and are selected from the group consisting of alanine, valine, leucine, isoleucine, glycine, cysteine, phenylalanine, tryptophan, and methionine.

7. The isolated nucleic acid molecule of claim 1 or 2 wherein said nucleic acid is ribonucleic acid.

8. The isolated nucleic acid molecule of claim 7 wherein said ribonucleic acid is mRNA.

9. A cell comprising the nucleic acid molecule of claim 1 or 2.

10. The cell of claim 9 wherein the cell is a plant cell.

11. The cell of claim 10 wherein the plant is a tree.

12. The cell of claim 11 wherein said tree is a poplar tree.

13. The cell of claim 9 wherein the cell further comprises a nucleic acid molecule encoding a promoter and wherein expression of the nucleic acid molecule encoding a polypeptide is controlled by the promoter.

14. The cell of claim 13 wherein the promoter is a CaMV 35 S promoter.

15. The cell of claim 13 wherein the promoter is a wound inducible promoter.

16. The cell of claim 13 wherein the promoter is a tissue-specific promoter.

17. An expression vector comprising the nucleic acid molecule of claim 1 or 2.

18. The expression vector of claim 17 wherein said expression vector is selected from the group consisting of a plasmid and a virus.

19. The expression vector of claim 17, wherein said expression vector further comprises a nucleic acid molecule encoding a promoter and wherein expression of the nucleic acid molecule encoding a polypeptide is controlled by the promoter.

20. The expression vector of claim 19 wherein the promoter is a CaMV 35S promoter.

21. The expression vector of claim 19 wherein the promoter is a wound inducible promoter.

22. An expression vector designated pWEA1.

23. An expression vector designated pWEA2.

24. The expression vector of claim 19 wherein the promoter is a tissue-specific promoter.

25. A cell comprising the expression vector of claim 17.

26. The cell of claim 25 wherein the cell is a plant cell.

27. The cell of claim 26 wherein the plant is a tree.

28. The cell of claim 27 wherein said tree is a poplar tree.

29. A transgenic plant comprising the nucleic acid molecule of claim 1 or 2.

30. The transgenic plant of claim 29 wherein the transgenic plant is a tree.

31. The transgenic plant of claim 30 wherein the tree is a poplar tree.

32. A seed produced by the transgenic plant of claim 29.

33. A seed which, upon germination, produces the transgenic plant of claim 29.

34. A seed comprising the nucleic acid molecule of claim 1 or 2.

35. A method of producing a plant having improved resistance to fungal or bacterial infestation, said method comprising:

introducing the nucleic acid molecule of claim 1 or 2 into a cell of a plant; and culturing the plant under conditions effective for expression of the nucleic acid molecule.

36. The method according to claim 35 wherein the plant is a tree.

37. The method according to claim 36 wherein the tree is a poplar tree.

38. A method of producing a plant cell useful for regeneration of a plant having increased fungal or bacterial resistance, said method comprising:

transforming a plant cell with the nucleic acid molecule of claim 1 or 2.

39. The method of claim 38 wherein the plant cell is derived from a tree.

40. The method of claim 39 wherein the tree is a poplar tree.

41. The method of claim 38 further comprising regenerating the transformed plant cell to form a transgenic plant.

42. A transgenic plant produced by the method of claim 41.

43. A seed produced by the transgenic plant of claim 42.

44. The isolated nucleic acid molecule of claim 15, wherein said nucleic acid molecule has a nucleic acid sequence selected from the group consisting of SEQ ID NO:15, SEQ ID NO:16, SEQ ID NO:17, SEQ ID NO:18, SEQ ID NO:19, and SEQ ID NO:20.

* * * * *

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
( A ) LENGTH: 18 amino acids
( B ) TYPE: amino acid
( C ) STRANDEDNESS: Not Relevant
( D ) TOPOLOGY: linear ( i i ) MOLECULE TYPE: peptide ( x i ) SEQUENCE DESCRIPTION: SEQ ID NO:1:

Met Ala Ser Arg Ala Ala Gly Leu Ala Ala Arg Leu Ala Arg Leu Ala
1               5                   1 0                 1 5

Leu Arg ( 2 ) INFORMATION FOR SEQ ID NO:2:

( i ) SEQUENCE CHARACTERISTICS:
( A ) LENGTH: 19 amino acids
( B ) TYPE: amino acid
( C ) STRANDEDNESS: Not Relevant
( D ) TOPOLOGY: linear ( i i ) MOLECULE TYPE: peptide ( x i ) SEQUENCE DESCRIPTION: SEQ ID NO:2:

Met Ala Ser Arg Ala Ala Gly Leu Ala Ala Arg Leu Ala Arg Leu Ala
1               5                   1 0                 1 5

Leu Arg Ala ( 2 ) INFORMATION FOR SEQ ID NO:3:

( i ) SEQUENCE CHARACTERISTICS:
( A ) LENGTH: 20 amino acids
( B ) TYPE: amino acid
( C ) STRANDEDNESS: Not Relevant
( D ) TOPOLOGY: linear ( i i ) MOLECULE TYPE: peptide ( x i ) SEQUENCE DESCRIPTION: SEQ ID NO:3:

Met Ala Ser Arg Ala Ala Gly Leu Ala Ala Arg Leu Ala Arg Leu Ala
1               5                   1 0                 1 5

Leu Arg Ala Leu
            2 0

( 2 ) INFORMATION FOR SEQ ID NO:4:

( i ) SEQUENCE CHARACTERISTICS:
( A ) LENGTH: 17 amino acids
( B ) TYPE: amino acid
( C ) STRANDEDNESS: Not Relevant
( D ) TOPOLOGY: linear ( i i ) MOLECULE TYPE: peptide ( x i ) SEQUENCE DESCRIPTION: SEQ ID NO:4:

Ala Ser Arg Ala Ala Gly Leu Ala Ala Arg Leu Ala Arg Leu Ala Leu
1               5                   1 0                 1 5

Arg (2) INFORMATION FOR SEQ ID NO:5:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:5:

```
Met  Val  Ser  Arg  Ala  Ala  Gly  Leu  Ala  Ala  Arg  Leu  Ala  Arg  Leu  Ala
 1                        5                         10                        15

Leu  Arg
```

(2) INFORMATION FOR SEQ ID NO:6:

(i) SEQUENCE CHARACTERISTICS:
        (A) LENGTH: 19 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:6:

```
Met  Val  Ser  Arg  Ala  Ala  Gly  Leu  Ala  Ala  Arg  Leu  Ala  Arg  Leu  Ala
 1                        5                         10                        15

Leu  Arg  Ala
```

(2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:7:

```
Met  Val  Ser  Arg  Ala  Ala  Gly  Leu  Ala  Ala  Arg  Leu  Ala  Arg  Leu  Ala
 1                        5                         10                        15

Leu  Arg  Ala  Leu
                20
```

(2) INFORMATION FOR SEQ ID NO:8:

(i) SEQUENCE CHARACTERISTICS:
        (A) LENGTH: 18 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:8:

```
Met  Ala  Ser  Arg  Ala  Ala  Gly  Leu  Ala  Arg  Arg  Leu  Ala  Arg  Leu  Ala
 1                        5                         10                        15

Arg  Arg
```

(2) INFORMATION FOR SEQ ID NO:9:

(i) SEQUENCE CHARACTERISTICS:
        (A) LENGTH: 19 amino acids
        (B) TYPE: amino acid
        (C) STRANDEDNESS: Not Relevant (D) TOPOLOGY: linear (ii) MOLECULE TYPE: peptide (xi) SEQUENCE DESCRIPTION: SEQ ID NO:9:

```
Met Ala Ser Arg Ala Ala Gly Leu Ala Arg Arg Leu Ala Arg Leu Ala
 1               5                  10                  15
Arg Arg Ala
```

(2) INFORMATION FOR SEQ ID NO:10:

(i) SEQUENCE CHARACTERISTICS:
  (A) LENGTH: 20 amino acids
  (B) TYPE: amino acid
  (C) STRANDEDNESS: Not Relevant
  (D) TOPOLOGY: linear (ii) MOLECULE TYPE: peptide (xi) SEQUENCE DESCRIPTION: SEQ ID NO:10:

```
Met Ala Ser Arg Ala Ala Gly Leu Ala Arg Arg Leu Ala Arg Leu Ala
 1               5                  10                  15
Arg Arg Ala Leu
                20
```

(2) INFORMATION FOR SEQ ID NO:11:

(i) SEQUENCE CHARACTERISTICS:
  (A) LENGTH: 18 amino acids
  (B) TYPE: amino acid
  (C) STRANDEDNESS: Not Relevant
  (D) TOPOLOGY: linear (ii) MOLECULE TYPE: peptide (xi) SEQUENCE DESCRIPTION: SEQ ID NO:11:

```
Met Ala Ala Arg Ala Ala Gly Leu Ala Ala Arg Leu Ala Ala Leu Ala
 1               5                  10                  15
Leu Arg
```

(2) INFORMATION FOR SEQ ID NO:12:

(i) SEQUENCE CHARACTERISTICS:
  (A) LENGTH: 19 amino acids
  (B) TYPE: amino acid
  (C) STRANDEDNESS: Not Relevant
  (D) TOPOLOGY: linear (ii) MOLECULE TYPE: peptide (xi) SEQUENCE DESCRIPTION: SEQ ID NO:12:

```
Met Ala Ala Arg Ala Ala Gly Leu Ala Ala Arg Leu Ala Ala Leu Ala
 1               5                  10                  15
Leu Arg Ala
```

(2) INFORMATION FOR SEQ ID NO:13:

(i) SEQUENCE CHARACTERISTICS:
  (A) LENGTH: 20 amino acids
  (B) TYPE: amino acid
  (C) STRANDEDNESS: Not Relevant
  (D) TOPOLOGY: linear (ii) MOLECULE TYPE: peptide (xi) SEQUENCE DESCRIPTION: SEQ ID NO:13:

```
Met Ala Ala Arg Ala Ala Gly Leu Ala Ala Arg Leu Ala Ala Leu Ala
```

Leu Arg Ala Leu
            20

(2) INFORMATION FOR SEQ ID NO:14:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Ser Arg Ala Ala Gly Leu Ala Ala Arg Leu Ala Arg Leu Ala Leu
 1               5                   10                  15

(2) INFORMATION FOR SEQ ID NO:15:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:15:

ATGGCNWSNM GNGCNGCNGG NYTNGCNGCN MGNYTNGCNM GNYTNGCNYT NMGN     54

(2) INFORMATION FOR SEQ ID NO:16:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:16:

ATGGCNWSNM GNGCNGCNGG NYTNGCNGCN MGNYTNGCNM GNYTNGCNYT NMGNGCNYTN     60

(2) INFORMATION FOR SEQ ID NO:17:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:17:

GCNWSNMGNG CNGCNGGNYT NGCNGCNMGN YTNGCNMGNY TNGCNYTNMG N     51

(2) INFORMATION FOR SEQ ID NO:18:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

ATGGCNWSNM GNGCNGCNGG NYTNGCNMGN MGNYTNGCNM GNYTNGCNMG NMGNGCNYTN     60

(2) INFORMATION FOR SEQ ID NO:19:

(i) SEQUENCE CHARACTERISTICS:
(A) LENGTH: 60 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:19:

ATGGCNGCNM GNGCNGCNGG NYTNGCNGCN MGNYTNGCNG CNYTNGCNYT NMGNGCNYTN    60

(2) INFORMATION FOR SEQ ID NO:20:

(i) SEQUENCE CHARACTERISTICS:
(A) LENGTH: 45 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:20:

WSNMGNGCNG CNGGNYTNGC NGCNMGNYTN GCNMGNYTNG CNYTN    45

(2) INFORMATION FOR SEQ ID NO:21:

(i) SEQUENCE CHARACTERISTICS:
(A) LENGTH: 188 base pairs
(B) TYPE: nucleic acid
(C) STRANDEDNESS: single
(D) TOPOLOGY: linear (ii) MOLECULE TYPE: DNA (xi) SEQUENCE DESCRIPTION: SEQ ID NO:21:

GGATCCGTCG ACAATATTCT CGAGGCCGCC ACCATGGCAA GTAGAGCCGC AGGTCTTGCC    60

GCACGGCTTG CCAGACTTGC ACTTCGGTAA CCATGGGTGA ATGTGTTAGA GGTAGATGCC   120

CAAGTGGTAT GTGTTGCTCC CAATTCGGTT ACTGTGGGAA AGGTCCAAAA TACTGCGGTT   180

AAGAGCTC   188

(2) INFORMATION FOR SEQ ID NO:22:

(i) SEQUENCE CHARACTERISTICS:
(A) LENGTH: 29 amino acids
(B) TYPE: amino acid
(C) STRANDEDNESS: Not Relevant
(D) TOPOLOGY: linear (ii) MOLECULE TYPE: peptide (xi) SEQUENCE DESCRIPTION: SEQ ID NO:22:

Met Gly Glu Cys Val Arg Gly Arg Cys Pro Ser Gly Met Cys Cys Ser
 1               5                  10                  15

Gln Phe Gly Tyr Cys Gly Lys Gly Pro Lys Tyr Cys Gly
             20                  25